United States Patent
Domb et al.

(10) Patent No.: US 10,774,176 B2
(45) Date of Patent: Sep. 15, 2020

(54) ALTERNATING AND SEMI-ALTERNATING POLY(ESTER-ANHYDRIDE) COPOLYMERS

(71) Applicant: DEXCEL PHARMA TECHNOLOGIES LTD., Or-Akiva (IL)

(72) Inventors: Abraham J. Domb, Jerusalem (IL); Michael Grishko, Nesher (IL); Ezra Hanuka, Nesher (IL); Ron Schlinger, Tel-Aviv (IL); Tal Hagigit, Yoshiya (IL)

(73) Assignee: DEXCEL PHARMA TECHNOLOGIES LTD., Or-Akiva (IL)

( * ) Notice: Subject to any disclaimer, the term of this patent is extended or adjusted under 35 U.S.C. 154(b) by 422 days.

(21) Appl. No.: 15/532,939

(22) PCT Filed: Dec. 17, 2015

(86) PCT No.: PCT/IB2015/002378
§ 371 (c)(1),
(2) Date: Jun. 2, 2017

(87) PCT Pub. No.: WO2016/097848
PCT Pub. Date: Jun. 23, 2016

(65) Prior Publication Data
US 2018/0043026 A1    Feb. 15, 2018

Related U.S. Application Data

(60) Provisional application No. 62/093,838, filed on Dec. 18, 2014.

(51) Int. Cl.
| | |
|---|---|
| *C08G 63/06* | (2006.01) |
| *C08G 67/04* | (2006.01) |
| *A61K 47/34* | (2017.01) |
| *A61K 9/14* | (2006.01) |
| *A61K 9/00* | (2006.01) |

(52) U.S. Cl.
CPC .............. *C08G 63/06* (2013.01); *A61K 9/146* (2013.01); *A61K 47/34* (2013.01); *C08G 67/04* (2013.01); *A61K 9/0024* (2013.01)

(58) Field of Classification Search
CPC ........ A61K 47/34; A61K 9/146; C08G 63/06; C08G 67/04
See application file for complete search history.

(56) References Cited

U.S. PATENT DOCUMENTS

| | | | |
|---|---|---|---|
| 4,414,381 A | 11/1983 | Griffin et al. | |
| 4,999,417 A | 3/1991 | Domb | |
| 5,010,167 A | 4/1991 | Ron et al. | |
| 5,109,107 A | 4/1992 | Vora et al. | |
| 5,171,812 A | 12/1992 | Domb | |
| 5,179,189 A | 1/1993 | Domb et al. | |
| 5,317,079 A | 5/1994 | Domb et al. | |
| 5,473,103 A | 12/1995 | Domb et al. | |
| 5,480,787 A | 1/1996 | Negishi et al. | |
| 5,565,188 A | 10/1996 | Wong et al. | |
| 5,626,862 A | 5/1997 | Brem et al. | |
| 5,648,096 A | 7/1997 | Gander et al. | |
| 5,756,652 A | 5/1998 | Storey et al. | |
| 5,846,565 A | 12/1998 | Brem et al. | |
| 5,859,271 A | 1/1999 | Franson et al. | |
| 6,025,410 A | 2/2000 | Moy et al. | |
| 6,303,138 B1 | 10/2001 | Peterson et al. | |
| 6,306,403 B1 | 10/2001 | Donovan | |
| 7,297,347 B2 | 11/2007 | Domb | |
| 7,749,539 B2 | 7/2010 | Domb | |
| 8,575,092 B2 | 11/2013 | Domb | |
| 2004/0161464 A1 | 8/2004 | Domb | |
| 2009/0111732 A1 | 4/2009 | Domb | |

FOREIGN PATENT DOCUMENTS

| | | |
|---|---|---|
| EP | 0598131 A1 | 5/1994 |
| EP | 0892022 A1 | 1/1999 |
| EP | 0952171 A3 | 10/1999 |
| WO | WO 1990/015586 | 12/1990 |
| WO | WO 1993/005096 | 3/1993 |
| WO | WO 1996/022270 | 7/1996 |
| WO | WO 1998/002171 | 1/1998 |
| WO | WO 1999/012990 | 3/1999 |
| WO | WO 2002/044232 | 6/2002 |
| WO | WO 2005/079861 | 9/2005 |
| WO | WO 2007/110694 | 10/2007 |

OTHER PUBLICATIONS

Domb, A.J., et al.; Journal of Biomedical Materials Research Part A, 2007, vol. 83A, p. 1138-1145.*
Bremer et al., Fatty Acid Oxidation and Its Regulation in Fatty Acid Metabolism and Its Regulation (Numa Ed.) 1984, Elsevier, New York, pp. 113-154.
Dang et al., Effects of GLIADEL® Wafer Initial Molecular Weight on the Erosion of Wafer and Release of BCNU, J. Cont. Rel. 1996, 42, pp. 83-92.
Domb et al., Absorbable Biopolymers Derived From Dimer Fatty Acids, J. Poly. Sci.: Part A: Poly. Chem. 1993, 31, pp. 1275-1285.
Domb et al., Biopolymers As Drug Carriers and Bioactive Macromolecules, Acta Polymer. 1998, 49(10-11), pp. 526-533.
Domb et al., Poly(anhydrides). 3. Poly(anhydrides) Based on Aliphatic-Aromatic Diacids, Macromol. 1989, 22, pp. 3200-3204.
Domb et al., Polyanhydrides in Handbook of Biodegradable Polymers (Domb et al., Eds.) Harwood Academic Publishers, 1997, pp. 135-159.

(Continued)

*Primary Examiner* — Robert S Jones, Jr.
(74) *Attorney, Agent, or Firm* — Brinks Gilson & Lione; Yuezhong Feng

(57) ABSTRACT

A copolymer characterized by alternating or semi-alternating ester and anhydride bonds, methods for its production and use thereof, particularly as a carrier for drug delivery, are described herein.

19 Claims, 12 Drawing Sheets

(56) References Cited

OTHER PUBLICATIONS

Domb et al., Polyanhydrides. I. Preparation of High Molecular Weight Polyanhydrides, J. Poly. Sci.: Part A: Poly. Chem. 1987, 25, pp. 3373-3386.

Domb et al., Proceedings of the 8$^{th}$ Polymer For Advanced Technologies International symposium, Sep. 2005, pp. 13-16.

Gopferich, Mechanism of Polymer Degradation and Elimination in Handbook of Biodegradable Polymers (Domb et al. Eds.) Harwood Academic Publishers, 1997, pp. 451-471.

Heller, Biodegradable Polymers in Controlled Drug Delivery, CRS Crit. Rev. Ther. Drug Carrier Syst. 1984, 1, pp. 39-90.

Hiremath et al., Biodegradable Poly (sebacic acid-co-ricinoleic ester anhydride) Tamoxifen Citrate Implants: Preparation and In Vitro Characterization. J. Appl. Poly. Sci. 2008, 107, pp. 2745-2754.

Hopfenberg, Controlled Release From Erodible Slabs, Cylinders, and Spheres in Controlled Release Polymeric Formulations (Paul et al., Eds.) ACS Symposium Series, Washington DC, 1976, 33, pp. 26-32.

Krasko et al., Gentamicin Extended Release From an Injectable Polymeric Implant, J. Cont. Release, 2007, 117, pp. 90-96.

Krasko et al., Hydrolytic Degradation of Ricinoleic-Sebacic-Ester-Anhydride Copolymers, Biomacro. 2005, 6(4), pp. 1877-1884.

Krasko et al., Poly(ester anhydride)s Prepared by the Insertion of Ricinoleic Acid onto Poly(sebacic acid), J. Poly. Sci.: Part A: Poly. Chem. 2003, 41(8), pp. 1059-1069.

Leong et al., Polyanhydrides For Controlled Release of Bioactive Agents, Biomat. 1986, 7(5), pp. 364-371.

Mader et al., In Vitro/in Vivo Comparison of Drug Release and Polymer Erosion From Biodegradable P(FAD-SA) Polyanhydries—a Noninvasive Approach by the Combined Use of Electron Paramagnetic Resonance Spectroscopy and Nuclear Magnetic Resonance Imaging, Pharm. Res. 1997, 14(6), pp. 820-826.

O'Hagan, Microparticles and Polymers for Mucosal Delivery of Vaccines, Adv. Drug Deliv. Rev. 1998, 34, pp. 305-320.

Park et al., Biodegradable Polyanhydride Devices of Cefazolin Sodium, Bupivacaine, and Taxol for Local Drug Delivery: Preparation, and Kinetics and Mechanism of In Vitro Release, J. Cont. Release, 1998, 52, pp. 179-189.

Rosen et al., Bioerodible Polyanhydrides For Controlled Drug Delivery, Biomat. 1983, 4, pp. 131-133.

Shikanov et al., Poly(sebacic acid-co-ricinoleic acid) Biodegradable Carrier for Paclitaxel: In vitro Release and In-Vivo Toxicity, J. Biomed. Mat. Res. A, 2004, 69(1), pp. 47-54.

Shikanov et al., Poly(sebacic acid-co-ricinoleic acid) Biodegradable Carrier For Paclitaxel—Effect of Additives J. Cont. Release, 2005, 105(1-2), pp. 52-67.

Shikanov et al., Poly(sebacic acid-co-ricinoleic acid) Biodegradable Injectable in Situ Gelling Polymer, Biomacromol. 2006, 7(1), pp. 288-296.

Teomim et al., Fatty Acid Terminated Polyanhydrides, J. Poly. Sci.: Part A: Poly. Chem. 1999, 37, pp. 3337-3344.

Teomim et al., Perivascular Delivery of Heparin for the Reduction of Smooth Muscle Cell Proliferation After Endothelial Injury, J. Cont. Release, 1999, 60, pp. 129-142.

Teomim et al., Ricinoleic Acid-Based Biopolymers, J. Biomed. Mater. Res. 1999, 45(3), pp. 258-267.

Tirosh et al., Oxidative Stress Effect on the Integrity of Lipid Bilayers is Modulated by Cholesterol Level of Bilayers, Chem. Phys. Lipids, 1997, 87, pp. 17-22.

EESR to European Application No. 15869415.8, dated Apr. 18, 2018, (7p).

* cited by examiner

Chemical shift (ppm)

Chemical shift (ppm)

ALTERNATING AND SEMI-ALTERNATING POLY(ESTER-ANHYDRIDE) COPOLYMERS

This application is the national phase application out of PCT/IB2015/002378, filed Dec. 17, 2015, which claims priority to U.S. Provisional Patent Application No. 62/093,838, filed Dec. 18, 2014, the entireties of both of which are hereby incorporated by reference.

FIELD OF THE INVENTION

The invention is directed to poly(ester-anhydride) copolymers having alternating or semi-alternating ester and anhydride bonds, and methods of making the same.

BACKGROUND OF THE INVENTION

There has been extensive research in the area of biodegradable matrices for controlled release of drugs. Biodegradable matrices for drug delivery are useful because they obviate the need for additional medical intervention for removal of non-degradable drug depleted devices. The ideal polymeric formulation for delivering drug in a controlled manner must possess a variety of attributes. The polymer should be compatible with biological tissues and should also be biodegradable, having degradation components that are non-toxic and easily eliminated. The polymer should be hydrophobic so that it maintains its integrity in physiological environments, and should have versatile and predictable degradation and drug release profiles for both hydrophilic and/or hydrophobic agents. Generally, the polymer should be in a liquid or gel form at room temperature to facilitate administration to a target delivery site in a patient, but should increase in viscosity after administration so that the polymer is not dislodged or dispersed from the delivery site. A preferred polymer should be stable under normal storage conditions over extended periods of time. Finally, a preferred polymer should be easy to prepare at low cost without the need for expensive reagents or apparatus.

Many biodegradable polymers have been evaluated for use as implantable controlled drug release matrices, including polyesters, polycarbonates, natural and synthetic polyamides, polyphosphate esters, polyphosphazenes and polyanhydrides.

While hundreds of different polyanhydride polymers have been reported, not many may be considered to be practical carriers for drugs. First, many are composed of synthetic aromatic or heterocyclic monomers, which present the risk of toxicity and slow elimination rate after degradation. Second, these polymers tend to be highly sensitive to heat and moisture, which makes them unstable even at 0-5° C., necessitating storage at −20° C. or below. Thus, it can be challenging to deliver products containing these polymers to hospitals and other end-users. One polyanhydride device in clinical use is the GLIADEL® brain implant, which is manufactured by Guilford Pharmaceuticals. This product requires constant storage at −20° C. because at higher temperatures, the material degrades, with the molecular weight of the polymer carrier dropping from 20,000-110,000 to below 20,000 Daltons, deleteriously affecting the drug release rate and also contributing to the rejection of the device. Many polyanhydrides are composed of linear aliphatic acids, making them both crystalline and fragile. Such compositions are impractical as they may fragment during shipment or use. Furthermore, the crystalline (or otherwise solid) matrices must be inserted into a patient using surgical techniques, rather than by less invasive injection or laparoscopic procedures.

Poly(ester-anhydrides) formed from ricinoleic acid and natural fatty diacids have been disclosed in U.S. Pat. Nos. 7,297,347 and 7,749,539 to Domb. These polymers may be admixed with a variety of bioactive agents including small drug molecules, peptides and proteins. The drug delivery compositions are administered to a patient in a liquid, gel or paste form and are able to release the incorporated bioactive agent over several weeks. Although the poly(ester-anhydrides) represent a significant advance in the field of biodegradable polymer matrices, several key issues remain to be overcome to obtain a robust, clinically useful material.

The hitherto known poly(ester-anhydrides) are composed of a random sequence of ricinoleic acid and fatty diacids, and as such, do not exhibit consistent stability and other properties over the bulk of the material and may also exhibit significant batch to batch variability. Unlike other fatty acids, which are monofunctional, ricinoleic acid is a bifunctional fatty acid with one hydroxyl group along its chain. This bifunctionality allows the incorporation of ricinoleic acid units into fatty diacids, such as a polysebacic acid (PSA) framework. The lipophilic side chains of ricinoleic acid increase lipophilicity, and also hinder hydrolytic degradation. Accordingly, the rate of hydrolysis of this poly(ester-anhydride) polymer can be appropriately controlled by the amount of ricinoleic acid units incorporated in the framework. However, if ricinoleic acid is incorporated into the polymer in a random sequence using the hitherto known synthetic methods, the thus obtained polymer may exhibit undesirable characteristics. For example, the polymer may exhibit increased sensitivity to hydrolysis and depolymerization, thereby contributing to the overall instability of the polymer.

In addition, improper or inadequate reaction conditions during synthesis may result in the formation of short polymer chains and oligomeric impurities. The short polymer chains tend to affect the rigidity and viscosity of the entire composition thereby leading to irreproducible physical and chemical characteristics of the obtained polymer.

There remains a strong need for stable liquid or gel polymeric formulations that can be administered into the tissue with versatility in polymer degradation and drug release profile. There further remains a need for a facile and robust method of preparing poly(ester-anhydride) copolymers suitable as carriers for drug delivery.

SUMMARY OF THE INVENTION

A synthetic method for the preparation of poly(ester-anhydride) copolymers has been developed. The synthetic method results in the formation of alternating and semi-alternating copolymers. Such product possesses enhanced stability properties. In currently preferred embodiments, the poly(ester-anhydride) is a copolymer of ricinoleic acid and sebacic acid.

The method is based in part on the finding that by allowing the reaction between activated dicarboxylic acid and a polyfunctional organic molecule containing at least two functional groups, such as hydroxyl and carboxylic acid, to proceed essentially to completion, so that all or substantially all of the polyfunctional organic molecules are consumed during the reaction, a copolymer having alternating or semi-alternating ester and anhydride bonds can be obtained. The obtained copolymer is characterized by reproducible product specifications including controlled viscosity and molecular weight. Furthermore, the copolymer is stable for months at room temperatures.

In one embodiment, there is provided a poly(ester-anhydride) copolymer having alternating or semi-alternating ester and anhydride bonds of Formula (1)

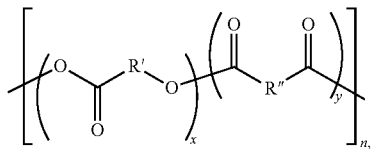

wherein R' and R" are independently selected from linear or branched $C_1$-$C_{40}$ alkyl, $C_2$-$C_{40}$ alkenyl, and $C_2$-$C_{40}$ alkynyl, and wherein each x and y is independently an integer from 1 to 5, provided that x+y is not greater than 6, and n is an integer from about 2 to about 1,000.

In another embodiment, a method for preparing a poly(ester-anhydride) copolymer having alternating or semi-alternating ester and anhydride bonds of Formula (1)

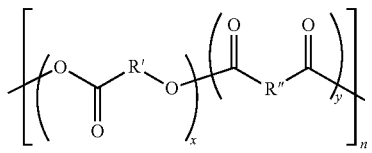

is provided,
the method including the steps of:
a) activating a compound of Formula (4)

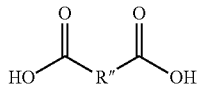

b) reacting the activated compound of Formula (4) obtained in step (a) with a compound of Formula (3)

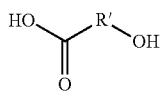

to give a repeating unit containing a compound of Formula (1a)

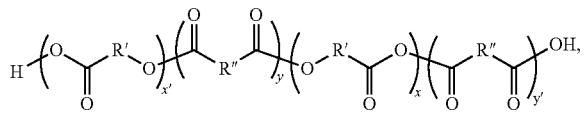

wherein R', R", x and y are as defined above and each x' and y' is independently an integer from 0 to 5, provided that x'+y' is not greater than 6; and
c) converting the repeating unit of step (b) to an alternating or semi-alternating poly(ester-anhydride) copolymer of Formula (1).

In yet another embodiment, a method for preparing a poly(ester-anhydride) copolymer having alternating or semi-alternating ester and anhydride bonds of Formula (1)

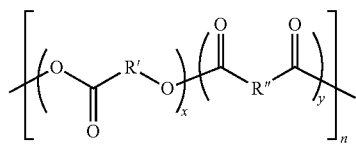

is provided,
the method including the steps of:
a) obtaining an activated compound of Formula (4)

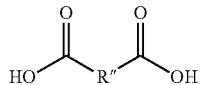

b) reacting the activated compound of Formula (4) of step (a) with a compound of Formula (3)

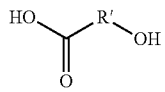

to give a repeating unit containing a compound of Formula (1a)

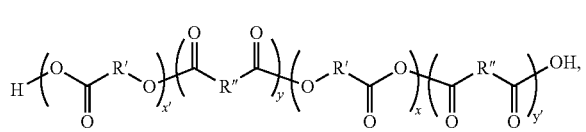

wherein R', R", x and y are as defined above and each x' and y' is independently an integer from 0 to 5, provided that x'+y' is not greater than 6; and
c) converting the repeating unit of step (b) to an alternating or semi-alternating poly(ester-anhydride) copolymer of Formula (1).

In one embodiment, the reaction between the activated compound of Formula (4) and a compound of Formula (3) in step (b) gives a repeating unit containing a compound of Formula (1b)

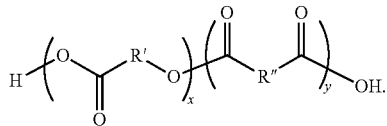

In some embodiments, a poly(ester-anhydride) copolymer having alternating or semi-alternating ester and anhydride bonds of Formula (1) is produced by the method described herein.

In other embodiments, R' is a branched $C_2$-$C_{40}$ alkenyl containing a $C_1$-$C_{10}$ alkyl-$C_2$-$C_{20}$ alkenyl, wherein the $C_1$-$C_{10}$ alkyl is α to the —O— of the ester bond. In particular embodiments, R' is a $C_6$ alkyl-$C_{11}$ alkenyl.

In some embodiments, R" is a linear $C_4$-$C_{22}$ alkyl. In other embodiments, R" is a linear $C_6$-$C_{10}$ alkyl. In particular embodiments, R" is a linear $C_8$ alkyl.

In certain embodiments, x and y, independently for each occurrence, is an integer selected from 1 and 2. Each possibility represents a separate embodiment. In accordance with these embodiments, a method is provided for preparing a poly(ester-anhydride) copolymer having alternating or semi-alternating ester and anhydride bonds of Formula (1) including the steps of:

a) activating a compound of Formula (4)

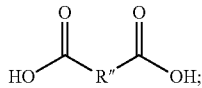

b) reacting the activated compound of Formula (4) obtained in step (a) with a compound of Formula (3)

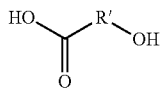

to give a repeating unit containing at least one of a compound of Formula (5), a compound of Formula (6) and a mixture thereof

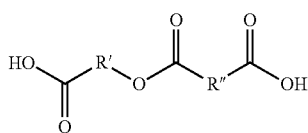

(5)

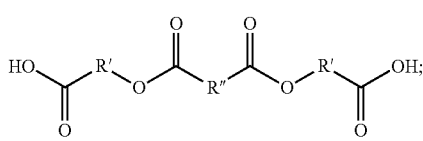

(6)

and c) converting the repeating unit of step (b) to an alternating or semi-alternating poly(ester-anhydride) copolymer of Formula (1).

In alternative embodiments, a method is provided for preparing a poly(ester-anhydride) copolymer having alternating or semi-alternating ester and anhydride bonds of Formula (1) including the steps of:

a) obtaining an activated compound of Formula (4)

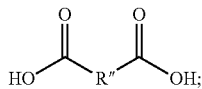

b) reacting the activated compound of Formula (4) of step (a) with a compound of Formula (3)

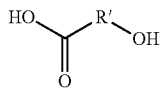

to give a repeating unit containing at least one of a compound of Formula (5), a compound of Formula (6) and a mixture thereof

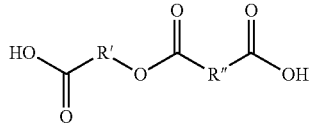

(5)

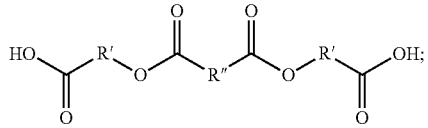

(6)

and c) converting the repeating unit of step (b) to an alternating or semi-alternating poly(ester-anhydride) copolymer of Formula (1).

In various embodiments, the molar ratio of the monomers of Formula (3) to the monomers of Formula (4) ranges from 5:1 and 1:5.

In further embodiments, the molar ratio of the monomers of Formula (3) to the monomers of Formula (4) is 2:1. In accordance with these embodiments, the copolymer comprises a repeating unit of Formula (6), namely a monomer of Formula (3), a monomer of Formula (4), and a monomer of Formula (3) linked by two consecutive ester bonds.

In additional embodiments, the molar ratio of the monomers of Formula (3) to the monomers of Formula (4) is 1:1. In accordance with these embodiments, the copolymer comprises a repeating unit of Formula (5), namely a monomer of Formula (3) and a monomer of Formula (4) linked by an ester bond.

In other embodiments, the molar ratio of the monomers of Formula (3) to the monomers of Formula (4) is 1.5:1. In accordance with these embodiments, the copolymer comprises two repeating units, a repeating unit of Formula (5) and a repeating unit of Formula (6). In one embodiment, the ratio between the first repeating unit and the second repeating unit is about 1:1.

In several embodiments, the poly(ester-anhydride) copolymer comprises an anhydride bond between each of the repeating units. It will be recognized by one of skill in the art that the repeating units are arranged in the copolymer in an alternating or semi-alternating order. Each possibility represents a separate embodiment of the copolymer.

According to some embodiments, the poly(ester-anhydride) copolymer comprises less than 10 mole %, preferably less than 5 mole %, and more preferably less than 2.5 mole % of two or more consecutive anhydride bonds between the monomeric units.

In certain embodiments, the activation of a compound of Formula (4) in step (a) is performed using an activating agent. Suitable activating agents are selected from the group consisting of acetic anhydride, propionic anhydride, phosgene, diphosgene, oxalyl chloride, acetyl chloride and thionyl chloride. Each possibility represents a separate embodiment.

In particular embodiments, the activating agent is acetic anhydride and the activated compound of Formula (4) is represented by the compound of Formula (4p)

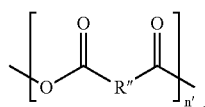

wherein n' is an integer from about 2 to about 500.

In various embodiments, the compound of Formula (3) and the activated compound of Formula (4) are reacted under conditions suitable to substantially consume all of the compounds of Formula (3). In accordance with these embodiments, the compound of Formula (3) is reacted with the activated compound of Formula (4) until at least about 90%, 95%, 97.5% or at least substantially all of the compounds of Formula (3) are consumed.

The reaction conditions suitable to substantially consume all of the compounds of Formula (3) may comprise heating, exposure to a vacuum, use of a catalyst or a combination thereof. In one embodiment, heating comprises performing the reaction at a temperature of about 120-200° C., preferably about 150-180° C., more preferably about 160-180° C. After the compound of Formula (3) is substantially consumed, the reaction mixture can be treated with an activating agent under conditions suitable to form the poly(ester-anhydride) copolymer. Suitable conditions include, for example, performing the reaction at a temperature of about 100-200° C., preferably about 110-180° C., more preferably about 130-150° C. Suitable activating agents include acetic anhydride, propionic anhydride, phosgene, diphosgene, oxalyl chloride, acetyl chloride and thionyl chloride. The method can be conducted at large scale using industrial conditions including, in particular, a vacuum of about 15 to about 30 mmHg.

The poly(ester-anhydride) copolymer having alternating or semi-alternating ester and anhydride bonds is stable for at least 6 months at room temperatures. In some embodiments, the poly(ester-anhydride) copolymer is stable for at least 12 months at room temperatures. In other embodiments, the poly(ester-anhydride) copolymer is stable for at least 18 months at room temperatures. In certain embodiments, the poly(ester-anhydride) copolymer is useful as a carrier for drug delivery.

In further embodiments, a composition containing a poly(ester-anhydride) copolymer having alternating or semi-alternating ester and anhydride bonds of Formula (1) and at least one agent is provided. In several embodiments, the at least one agent is a pharmaceutical agent, a diagnostic agent, a cosmetic agent and/or a nutraceutical agent. Each possibility represents a separate embodiment of the composition. In particular embodiments, the at least one agent is a pharmaceutical agent. In accordance with these embodiments, the composition is used as a medicament or device for therapy.

Further embodiments and the full scope of applicability of the copolymer, composition or method will become apparent from the detailed description given hereinafter. However, it should be understood that the detailed description and specific examples, while indicating preferred embodiments of the compositions and methods of making and using, are given by way of illustration only, since various changes and modifications within the spirit and scope of the invention will become apparent to those skilled in the art from this detailed description.

BRIEF DESCRIPTION OF THE DRAWINGS

FIG. 5A: At 140° C. for 1 hour; FIG. 5B: At 175° C. for 4 hours.

FIGS. 9B, 9D, and 9F are zoom ins of the anhydride and ester regions showing the relative ratios of the designated protons.

FIG. 11A shows the stability studies for 18 months of (RA-SA) alternating or semi-alternating copolymer under three conditions: −20° C., 5° C., and 25° C.+60% relative humidity. FIG. 11B shows a comparison of the percent drop in molecular weight of three polymers (polysebacic acid (PSA; circles), previously synthesized RA-SA polymer by Krasko et al. (squares), and polymer synthesized though the currently disclosed method (triangles) at 25° C.+60% relative humidity within a 100 day period. FIG. 11C shows a comparison of the percent drop in molecular weight of the three polymers (PSA; circles), previously synthesized RA-SA polymer by Krasko et al. (squares), and polymer synthesized though the currently disclosed method (triangles) in chloroform within a 24 hour period.

DETAILED DESCRIPTION OF THE INVENTION

Figure 1:
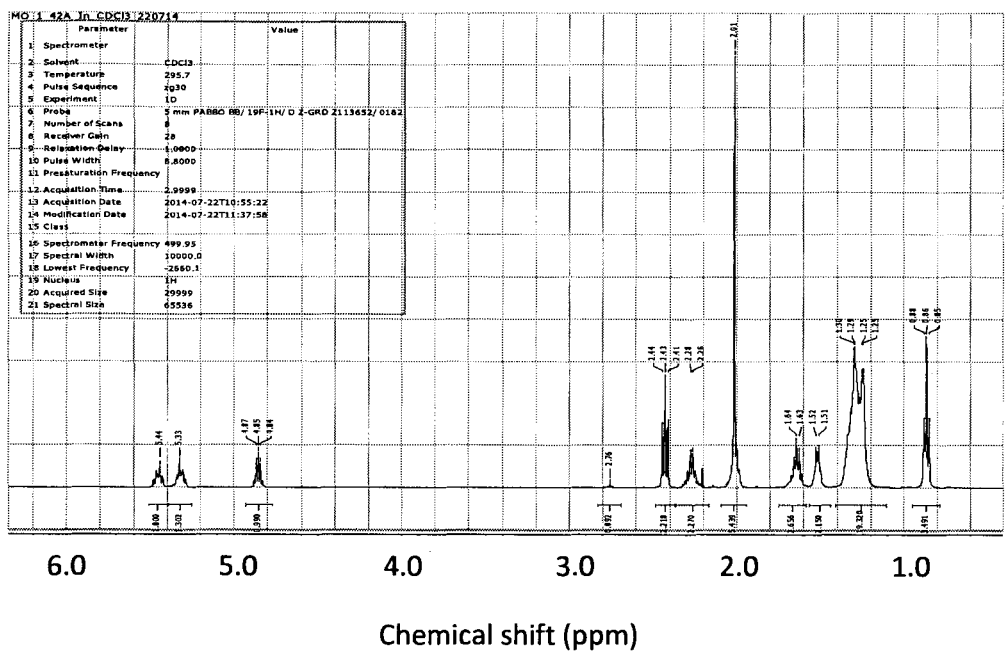
FIG. 1 shows the $^1$H-NMR spectrum of a polymer synthesized from ricinoleic acid (RA) by activation with acetic anhydride followed by polycondensation under heat and vacuum.

A poly(ester-anhydride) which is characterized by alternating or semi-alternating ester and anhydride bonds and process of synthesis thereof is provided. The poly(ester-anhydride) is produced from aliphatic dicarboxylic acid and hydroxy acid in a one-pot synthesis.

According to certain aspects and embodiments, there is provided a synthetic route for the synthesis of poly(ricinoleic acid-sebacic acid) copolymer having alternating or semi-alternating ester and anhydride bonds. The synthesis of poly(ricinoleic acid-sebacic acid) copolymer involves the reaction of the hydroxy acid (ricinoleic acid) with polysebacic acid (polysebacic anhydride). Initially, a nucleophilic attack of the ricinoleic acid cleaves the anhydride bonds of polysebacic acid, to introduce new ester bonds. Then, acetic anhydride is used to activate the carboxylic acids, followed by the final polycondensation under heat and vacuum to form the poly(ricinoleic acid-sebacic acid) copolymer. Unexpectedly, it has now been discovered that polycondensation before the complete esterification may lead to polymeric blocks resulting in a relatively unstable copolymer. By allowing the esterification to be completed such that substantially all ricinoleic acid is consumed before polycondensation, a polymer having alternating units of ricinoleic acid and sebacic acid can be obtained.

According to some aspects and embodiments, a method is provided for producing poly(ester-anhydride) copolymers, such as poly(ricinoleic acid-sebacic acid) copolymer, the method comprises the complete consumption of ricinoleic acid during the esterification step. Once all ricinoleic acid is reacted to form ester bonds, the final polymer may be synthesized by polymeric melt condensation so that the relative percentages of ester units as well as their location within the polymer sequence can be controlled. This is afforded by the formation of small repeating units (such as dimeric and/or trimeric units) prior to condensation reaction in the final step of polymerization. By changing the ratio of ricinoleic acid to sebacic acid as well as the reaction conditions, the structure of the final polymer is substantially controlled. Thus, a reproducible synthetic method is provided for synthesizing periodic or semi-periodic poly(ester-anhydride) copolymer containing alternating or semi-alternating ester and anhydride bonds.

A. Definitions

The term "aliphatic group" refers to a straight-chain, branched-chain, or cyclic hydrocarbon groups and includes saturated and unsaturated aliphatic groups which may be unsubstituted or substituted by one or more groups selected from halogen, ether, amine, aryl and heteroaryl. Each possibility represents a separate embodiment of the polymer.

The term "alkyl group" refers to a straight-chain, branched-chain, and cyclic hydrocarbon groups. Alkyl groups are further characterized in that they do not contain any carbon-carbon double or carbon-carbon triple bonds. The term "cycloalkyl group" defines a subset of alkyl groups which is characterized by the presence of at least one ring. The alkyl group can be unsubstituted or substituted through available carbon atoms with one or more groups defined hereinabove for aliphatic group.

The term "alkenyl group" refers to a straight-chain, branched-chain, and cyclic hydrocarbon groups, further having at least one carbon-carbon double bond ("alkene"). It is contemplated that the carbon-carbon double bond encompasses all configurations, including cis and trans configurations, independently at each occurrence. The term "cycloalkenyl group" defines a subset of alkenyl groups which are characterized by the presence of at least one ring, however, the terms "cycloalkenyl" and "alkenyl," in the absence of specific language to the contrary, exclude groups containing one or more aromatic rings. The alkenyl group can be unsubstituted or substituted through available carbon atoms with one or more groups defined hereinabove for aliphatic group.

The term "alkynyl group" refers to a straight-chain, branched-chain, and cyclic hydrocarbon groups, further having at least one carbon-carbon triple bond ("alkyne"). The term "cycloalkynyl group" defines a subset of alkynyl groups which is characterized by the presence of at least one ring. The alkynyl group can be unsubstituted or substituted through available carbon atoms with one or more groups defined hereinabove for aliphatic group.

B. Poly(Ester-Anhydride) Copolymers

Poly(ester-anhydride) copolymers are disclosed herein. The poly(ester-anhydride) copolymers contain an alternating or semi-alternating sequence of monomer units, and as such exhibit increased stability relative to random poly(ester-anhydride) co-polymers. The copolymers may be represented by the compound of Formula (1):

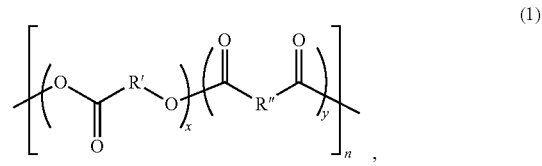

wherein R' and R" are independently selected from linear or branched $C_1$-$C_{40}$ alkyl, $C_2$-$C_{40}$ alkenyl, and $C_2$-$C_{40}$ alkynyl, and wherein each x and y is independently an integer from 1 to 5 provided that x+y is not greater than 6, and n is an integer from about 2 to about 1,000.

In certain embodiments, x+y is equal to 2, 3 or 5. Each possibility represents a separate embodiment of the polymer. In preferred embodiments, x is 1 and y is 1, or x is 2 and y is 1. Each possibility represents a separate embodiment of the polymer.

The poly(ester-anhydride) copolymer contains an alternating or semi-alternating sequence of monomeric units. In some embodiments, the alternating sequence comprises a repeating trimeric unit. In other embodiments, the semi-alternating sequence comprises a repeating dimeric unit. In yet other embodiments, the semi-alternating sequence comprises two repeating units, i.e. a trimeric unit and a dimeric unit.

In one embodiment, the alternating sequence contains the following repeating trimeric unit:

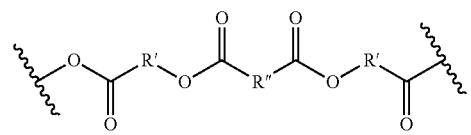

The above formula may further be designated by the formula -(ABA)-, wherein A represents the R' containing monomeric unit, and B represents the R" containing monomeric unit. The monomeric units are linked by two consecutive ester bonds. Using this formula, the copolymer has an alternating sequence which may be depicted:

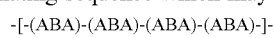

In another embodiment, the semi-alternating sequence of the poly(ester-anhydride) copolymer contains the following repeating dimeric unit in which the monomeric units are linked by an ester bond:

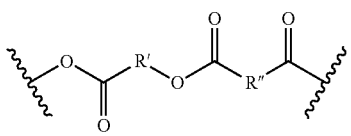

In accordance with these embodiments, the poly(ester-anhydride) copolymer comprises semi-alternating sequence of repeating dimeric units which may be -(A-B)-(A-B)- ("head-to-tail"); -(B-A)-(A-B)- ("head-to-head"); -(A-B)-(B-A)- ("tail-to-tail") or a combination thereof. In certain embodiments, a co-polymer containing the repeating dimeric unit comprises an equivalent amount of the-three linkages described-above. It will be recognized by one of skill in the art that the choice of R' and R" may result in steric hindrance thereby favoring one of the three linkages described above.

The poly(ester-anhydride) may comprise a sequence of the trimeric unit, a sequence of the dimeric unit, or a sequence of a mixture of the trimeric and dimeric units. As used herein, "a poly(ester-anhydride) containing a sequence of the trimeric unit" refers to a polymer in which at least 90%, preferably at least 95%, more preferably at least 97.5%, and even more preferably at least substantially all of its sequence is composed of the repeating trimeric unit. Similarly, the phrase "a poly(ester-anhydride) containing a sequence of the dimeric unit" refers to a polymer in which at least 90%, preferably at least 95%, more preferably at least 97.5%, and even more preferably at least substantially all of its sequence is composed of the repeating dimeric unit. The units may be arranged in a periodic or semi-periodic sequence thereby resulting in a poly(ester-anhydride) containing alternating or semi-alternating monomeric units.

In some aspects and embodiments, where x and y, independently for each occurrence, is an integer selected from 1 and 2, the poly(ester-anhydride) of Formula (1) is characterized by the substantial absence of two or more consecutive anhydride bonds between the monomeric units along its structure. In accordance with these embodiments, the poly(ester-anhydride) comprises less than about 10 mole %, preferably less than about 5 mole %, and more preferably less than about 2.5 mole % of two or more consecutive anhydride bonds between the monomeric units along its structure.

In certain embodiments, the poly(ester-anhydride) has the structure of Formula (2):

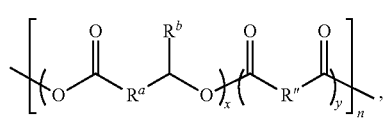

Formula (2)

wherein R", x, y and n are as defined above, $R^a$ is a $C_2$-$C_{20}$ alkenyl, and $R^b$ is a $C_1$-$C_{10}$ alkyl. In currently preferred embodiments, $R^a$ is a $C_{10}$ alkenyl, and $R^b$ is a $C_6$ alkyl.

For certain embodiments in which $R^a$ is $C_2$-$C_{20}$ alkenyl, $R^a$ may be represented by the formula:

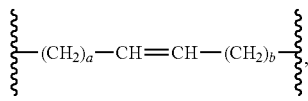

wherein a and b are selected from 0-18, provided that a+b is equal to or less than 18. The $(CH_2)_a$ unit is further connected to the carbonyl and the $(CH_2)_b$ unit is further connected to the oxygen atom. The double bond may have a cis or trans configuration. Each possibility represents a separate embodiment of the polymer. In preferred embodiments, a is selected from 1-12, preferably 1-10, more preferably 2-10, even more preferably 4-10, and b is selected from 0-6, preferably 1-6, and even more preferably 1-4. In certain preferred embodiments, a is 7, b is 2, and the olefin is in the cis configuration.

In some embodiments, R" is a linear, unsubstituted $C_1$-$C_{12}$ alkyl group, preferably $C_2$-$C_{10}$, more preferably $C_4$-$C_{10}$, and even more preferably a linear, unsubstituted $C_6$-$C_8$ alkyl group. In preferred embodiments, R" is an unsubstituted, linear $C_8$ alkyl group, i.e., —$(CH_2)_8$—.

The poly(ester-anhydride) copolymer exhibits unexpected hydrolytic and storage stability, even when stored at 5° or 25° C. and 60% relative humidity. It is believed that stability may be afforded by the periodic or semi-periodic sequence of the monomeric units so that the anhydride bonds are sterically hindered and protected by the hydrophobic side chains of a branched compound of Formula (3). It is further contemplated that the steric hindrance of the hydrophobic side chains prevents the anhydride bonds from going through interchange in a depolymerization process. The stability may be assessed by placing the polymer in glass syringes and storing the syringes, optionally packed in sealed aluminum bags, at various temperatures and relative humidities. The syringes may or may not be subjected to γ-irradiation prior to storage. The relative stability may be evaluated by measuring adsorbed water content, molecular weight and polydispersity index.

In certain embodiments, the adsorbed water content of the polymer is increased in less than about 1%, less than about 0.5%, less than about 0.2% or even less than about 0.1%, when the polymer is stored at 25°/60% RH, 5° or −20° C. for 6 months, preferably for 12 months and more preferably for 18 months. In other embodiments, the molecular weight of the polymer is decreased in less than about 25%, less than about 20%, less than about 15% or even less than about 10%, when the polymer is stored at 25°/60% RH, 5° or −20° C. for 6 months, preferably for 12 months and more preferably for 18 months.

The poly(ester-anhydride) copolymers may have molecular weights in the range of from about 1,000 to about 50,000 Daltons depending on the polymerization conditions and the ratio between the components of the starting materials. The determination of molecular weight can be performed as is known in the art, for example using gel-permeation chromatography (GPC). The viscosity of the obtained copolymer can be adjusted according to its methods of use. In particular embodiments, the copolymer is in liquid, semi-liquid or gel form at room temperatures thus being particularly suitable for administration via injection.

C. Methods of Preparation

The poly(ester-anhydride) copolymer may be prepared from a hydroxy-acid of Formula (3) and a diacid of Formula (4):

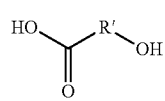

Formula (3)

-continued

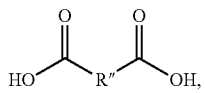

Formula (4)

wherein R' and R" are as defined above. By controlling the relative ratio of the compounds of Formula (3) and Formula (4) as well as the reaction conditions, either an alternating or semi-alternating poly(ester-anhydride) may be obtained. In one embodiment, the molar ratio of the monomers of Formula (3) to the monomers of Formula (4) ranges from 5:1 and 1:5. In other embodiments, the molar ratio of the monomers of Formula (3) to the monomers of Formula (4) is 2:1. In accordance with these embodiments, the copolymer has an alternating sequence containing a repeating trimeric unit as detailed above. In yet other embodiments, the molar ratio of the monomers of Formula (3) to the monomers of Formula (4) is 1:1. In accordance with these embodiments, the copolymer has a semi-alternating sequence containing a repeating dimeric unit as detailed above. In additional embodiments, the molar ratio of the monomers of Formula (3) to the monomers of Formula (4) is 1.5:1. In accordance with these embodiments, the copolymer has a semi-alternating sequence containing two repeating units containing a 1:1 ratio of a repeating trimeric unit and a repeating dimeric unit as detailed above. It will be recognized by one of skill in the art that other stoichiometric ratios may also be employed according to the method to provide alternating and/or semi-alternating copolymer.

The hydroxy-acid of Formula (3) and the diacid of Formula (4) can be obtained from readily available commercial suppliers or synthesized or extracted by standard methods known to one skilled in the art of chemical synthesis. In one embodiment, the hydroxy-acid of Formula (3) is a hydroxy fatty acid. Suitable hydroxyl acids include, but are not limited to, ricinoleic acid, hydroxyl stearic acid, γ-hydroxy fatty acid such as 10-hydroxy dodecanoic acid and the like. Each possibility represents a separate embodiment. The hydroxy fatty acids can be obtained from a natural or synthetic source. In a specific embodiment, the hydroxy-acid of Formula (3) is ricinoleic acid. In another specific embodiment, the ricinoleic acid is produced from castor oil as described in U.S. Pat. Nos. 7,297,347, 7,749,539 and 8,575,092, the content of each of which is hereby incorporated by reference.

The dicarboxylic acid (diacid) of Formula (4), according to certain embodiments of the method, is selected from the group consisting of dodecanedioic acid, undecanedioic acid, sebacic acid, azelaic acid, suberic acid, pimelic acid, adipic acid, glutaric acid, succinic acid, and diabolic acids. Each possibility represents a separate embodiment. In a specific embodiment, the dicarboxylic acid of Formula (4) is sebacic acid. In the first step, the diacid of Formula (4) is reacted with an activating agent to give a compound of Formula (4a):

Formula (4a)

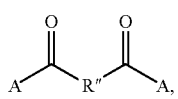

wherein R" is as defined above, and A is selected from, for example: Cl, ClCOO, CH$_3$—COO and CH$_3$CH$_2$COO. Each possibility represents a separate embodiment. The activating agent may be any compound that enhances the reactivity of the carbokylic acid to anhydride formation. Suitable activating agents include, but are not limited to, acetic anhydride, propionic anhydride, phosgene, diphosgene, oxalyl chloride, acetyl chloride and thionyl chloride. Each possibility represents a separate embodiment. In one embodiment, the activating agent is acetic anhydride.

In certain embodiments, the reaction of the compound of Formula (4) with an activating agent produces a polyanhydride of Formula (4p):

Formula (4p)

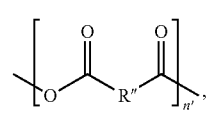

wherein R" is as defined above, and n' is an integer selected from about 2 to about 500, preferably from about 5 to about 250.

Alternatively, the activated compound of Formula (4a) or (4p) can be obtained e.g. from commercial sources. It will be recognized by one of skill in the art that obtaining the activated compound of Formula (4a) or (4p) from commercial sources obviate the need for the step of activating a compound of Formula (4) in the method disclosed herein.

The compound of Formula (4a), (4p) or mixture thereof is then reacted with the hydroxy acid of Formula (3) to provide, for example, a repeating unit containing a compound of Formula (1a):

(1a)

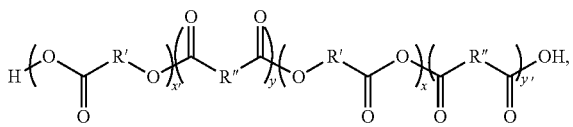

wherein R', R", x and y are as defined above and each x' and y' is independently an integer from 0 to 5 provided that x'+y' is not greater than 6. It is to be understood that although the Formulae are drawn in a specific configuration, it is contemplated that the polymer encompasses all configurations, independently at each occurrence. It will be recognized by one of skill in the art that each monomeric unit may be linked to another monomeric unit through ester or anhydride bond and that the compound of Formula (1a) has carboxylic acid end groups. In particular embodiments, the compound of Formula (4a), (4p) or mixture thereof is reacted with the hydroxy acid of Formula (3) to provide, for example a-repeating unit containing a compound of Formula (1b)

Formula (1b)

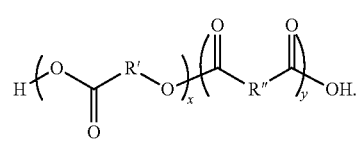

When the molar ratio of the compounds of Formula (4a) or the anhydride bonds in Formula (4p) to the compounds of Formula (3) is in the range of 2:1 to 1:2, the reaction provides a repeating unit containing a compound of Formula (5), a compound of Formula (6), or a mixture thereof:

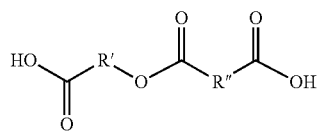
Formula (5)

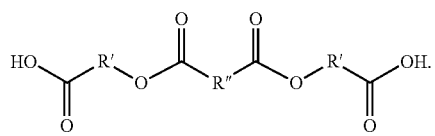
Formula (6)

The compounds of Formula (4a) and (4p) are reacted with the compound of Formula (3) under conditions sufficient to form an ester bond. According to certain aspects and embodiments, the esterification may be conducted by applying heat, vacuum or combinations thereof for a period of time sufficient so that the compound of Formula (3) is substantially consumed. The reaction is preferably conducted at a temperature of about 120-200° C., preferably about 150-180° C., and even more preferably at a temperature of about 160-180° C. Generally, the reaction is carried out for a period of several hours, depending on the batch size, mixing, reaction vessel and the ratio of the components of the starting materials.

The compounds of Formula (4a) and (4p) are reacted with the compound of Formula (3) so that at least 90% of the compound of Formula (3) is consumed in the reaction. Preferably, at least 95% of the compound of Formula (3) is consumed, more preferably at least 97.5% is consumed, and most preferably substantially all of the compound of Formula (3) is consumed. In one embodiment, the formed polymer is characterized by having less than about 2% acetylated terminus of the compound of Formula (3). For some embodiments that include the compound of Formula (4p) in certain amounts, it is preferred that at least 95% of the compound of Formula (4p) is consumed, more preferably at least 97.5% is consumed, and most preferably substantially all of the compound of Formula (4p) is consumed. The consumption of the compound of Formula (3) or Formula (4p) can be monitored using analytical techniques such as $^1$H or $^{13}$C NMR, mass spectroscopy, FT-IR, UV-VIS, or chromatography quantification as is known in the art. In particular embodiments, the consumption is monitored using $^1$H NMR by showing the disappearance of the peak which corresponds to the proton located at the carbon attached to the hydroxyl group.

The reaction mixture is then treated with an activating agent under conditions sufficient to form the poly(ester-anhydride) copolymer. Suitable activating agents include, but are not limited to, acetic anhydride, propionic anhydride, phosgene, diphosgene, oxalyl chloride, acetyl chloride and thionyl chloride. Each possibility represents a separate embodiment. In one embodiment, the activating agent is acetic anhydride. The reaction mixture may be heated, optionally with the application of vacuum, for a period of time sufficient to form the poly(ester-anhydride) copolymer having the desired molecular weight. The reaction is preferably conducted at a temperature of about 100-200° C., preferably about 110-180° C., and even more preferably at a temperature of about 130-150° C. For embodiments in which vacuum is applied, it is preferred that the vacuum is from 0.01 to about 100 mm Hg, preferably from about 0.5 to about 50 mm Hg, and even more preferably from about 15 to about 30 mm Hg, which is the vacuum range available in industrial settings for large scale equipment.

It will be recognized by one of skill in the art that the reactions disclosed herein can be performed such that the reagents are also used as solvents thereby obviating the need for the addition of solvents. Alternatively, solvents can be added. In accordance with these embodiments, solvents may include any solvent known in the art such as protic and aprotic solvents provided they do not interfere or alter the chemistry of the reaction(s). Non-limiting examples of suitable solvents include aliphatic hydrocarbon solvents, aromatic solvents, ether solvents, ester solvents, chlorinated hydrocarbons, protic polar solvents, aprotic polar solvents, mixed solvents, ionic liquids thereof and the like, and any mixtures thereof. Each possibility represents a separate embodiment of the method.

The work-up treatment in each step can be applied by a typical method, wherein isolation and purification is performed as necessary by selecting or combining conventional methods, such as precipitation in non-solvent, extraction, crystallization, recrystallization, distillation, partitioning, chromatography, preparative HPLC and the like. Each possibility represents a separate embodiment of the method.

As contemplated herein, there is provided a new process for producing poly(ester-anhydrides) copolymers having alternating or semi-alternating ester and anhydride bonds, as a one pot synthesis which may be performed on a manufacturing scale from the compounds of Formulae (3) and (4). The process can be performed at relatively low industrial vacuum. An exemplary, non-limiting process for producing poly(ester-anhydride) form ricinoleic acid and sebacic acid is illustrated in Scheme 1 below:

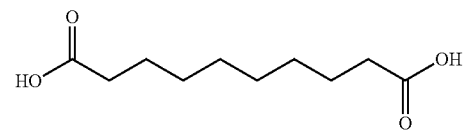

Step 2 | Acetic anhydride

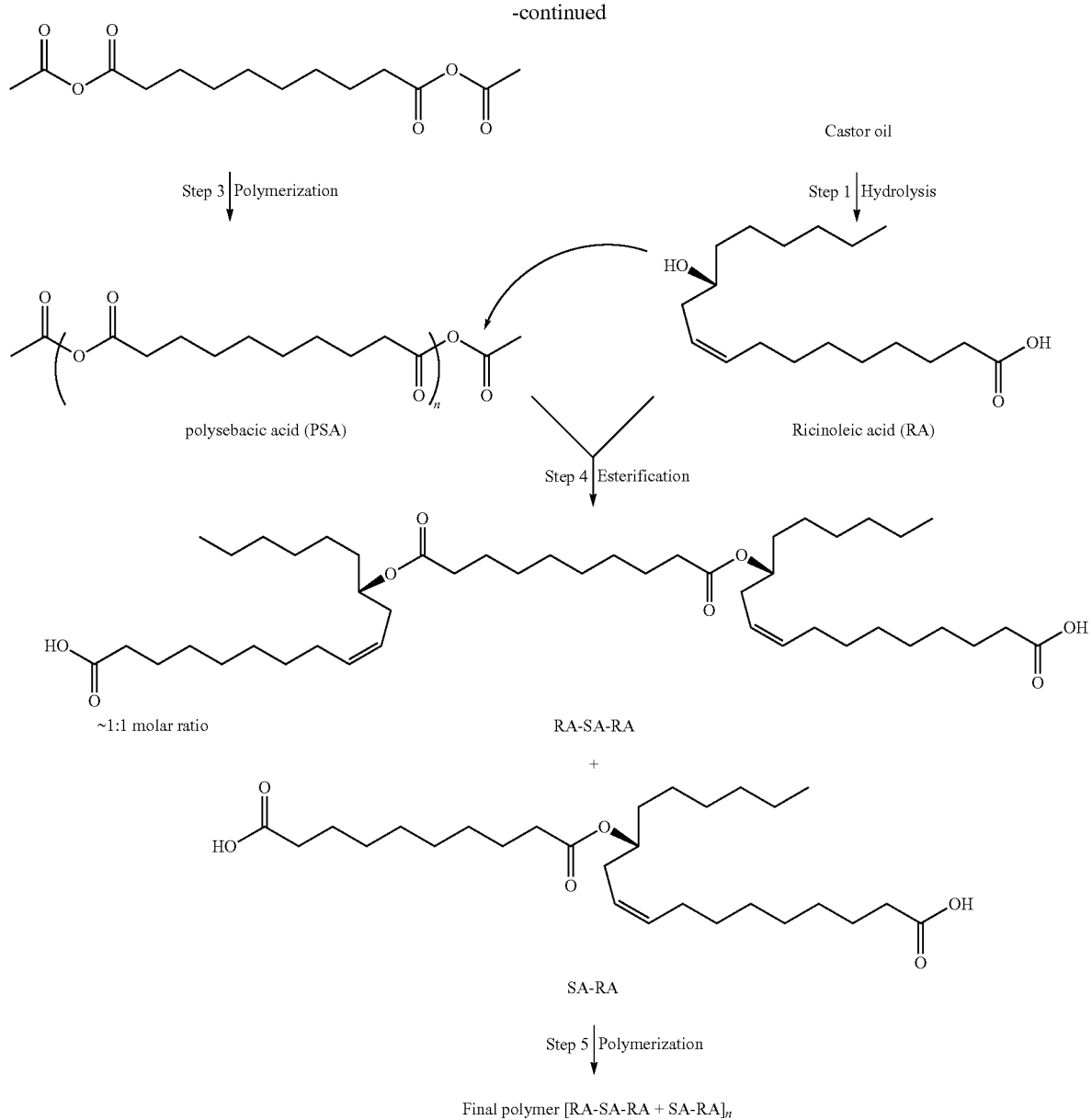

D. Methods of Use

The copolymer disclosed herein can be used in pharmaceutical, cosmetic or nutraceutical industry. In one embodiment, the copolymer is useful clinically, per se. In specific embodiments, the copolymer can be used to deliver therapeutic, diagnostic, and/or prophylactic agents. Each possibility represents a separate embodiment of the composition.

There is provided a composition including the copolymer as described herein and at least one agent. Exemplary drug agents useful for forming the composition described herein include, but are not limited to, analeptic agents; analgesic agents; anesthetic agents; antacid agents; antiasthmatic agents; antiarthritic agents; antibacterial agents; anticancer agents; anticholinergic agents; anticonvulsant agents; antidepressant agents; antidiabetic agents; antidiarrheal agents; antiemetic agents; anihelminthic agents; antihistamines; antihyperlipidemic agents; antihypertensive agents; anti-infective agents; anti-inflammatory agents; antimigraine agents; antineoplastic agents; antiparkinsonism drugs; antipruritic agents; antipsychotic agents; antipyretic agents; antispasmodic agents; antitubercular agents; antiulcer agents; antiviral agents; anxiolytic agents; appetite suppressants (anorexic agents); attention deficit disorder and attention deficit hyperactivity disorder drugs; cardiovascular agents including calcium channel blockers, antianginal agents, central nervous system ("CNS") agents, beta-blockers and antiarrhythmic agents; central nervous system stimulants; diuretics; genetic materials; hormonolytics; hypnotics; hypoglycemic agents; immunosuppressive agents; muscle relaxants; narcotic antagonists; nicotine; nutritional agents; parasympatholytics; peptide drugs; protein drugs; psychostimulants; sedatives; sialagogues; steroids; smoking cessation agents; sympathomimetics; tranquilizers; vasodilators; vaccines; beta-agonist; tocolytic agents; and mixtures thereof. Each possibility represents a separate embodiment of the composition. In one embodiment, the active agent is an anticancer agent, such as paclitaxel or methotrexate. In another embodiment, the active agent is an antibiotic, such as gentamicin, chlorhexidine or pharmaceutically acceptable salts thereof. In yet another embodiment, the active agent is an anesthetic agent, such as bupivacaine. In still another embodiment, the active agent is a peptide, protein or polysaccharide, such as a growth factor or heparin.

An effective amount of these agents can be determined by one of ordinary skill in the art. Factors to consider in determining a therapeutically effective amount include age, weight and physical condition of the person to be treated; type of agent used, type of polymer used; and desired release rate. Typically, the concentration of the active agent is from about 1% to about 90% by weight of the composition, preferably from about 5% to about 60% by weight of the composition, more preferably from about 5% to about 30% by weight of the composition, and even more preferably from about 5% to about 20% by weight of the composition.

The polymeric compositions described herein can be used as degradable carriers for treating local diseases such as cancer, bacterial and fungi local infections and pain. Site-specific chemotherapy that provides high drug concentrations for an extended time period in the diseased site is an effective way of treating remnant infected cells after resection of the infected area such as solid tumors.

Typically, the compositions are administered by injection and/or implantation, intramuscularly, subcutaneously, intraperitoneally, intracranially, and/or intratumor (before, during or after tumor resection). Each possibility represents a separate embodiment. The compositions may be inserted into cavities or any organ or tissue within a subject in need thereof to afford local and/or systemic therapy. The compositions are liquid, gel or pastes at room temperatures such that they can be injected or implanted without the need for additives. However, additives can be added e.g. in order to reduce the viscosity and/or improve the injectability of the compositions as needed. The compositions may be spread on the surface of different body tissues and/or mucosa and may be administered in adjunct to a surgical procedure.

It is contemplated that the compositions disclosed herein afford the long term drug delivery to specific diseased body sites for the treatment of local infections such as osteomyelitis-bone infection, for inducing local anesthetic delivery for cancer or AIDS patients and for inducing controlled tissue growth such as for treating restenosis and keloids, or for reducing the size of cancer tumors.

The polymers can also be used as coatings on implantable medical devices, such as stents, as surgical sealants or as barriers for the reduction of organ to organ adhesion.

In one embodiment, a method is provided for treating or preventing local infection by administering to a subject in need thereof a composition including the poly(ester-anhydride) copolymer and a therapeutically effective amount of an antibiotic agent. In particular embodiments, the subject is a mammal, preferably a human. In other embodiments, the composition is intended for veterinary use. In certain embodiments, use of the poly(ester-anhydride) copolymer and a therapeutically effective amount of an antibiotic agent for the preparation of a medicament for treating or preventing local infection is provided. In further embodiments, there is provided a composition including the poly(ester-anhydride) copolymer and a therapeutically effective amount of an antibiotic agent for use in treating or preventing local infection. The term "treating" as used herein refers to abrogating, inhibiting, slowing or reversing the progression of a disease, ameliorating clinical symptoms of a disease or preventing the appearance of clinical symptoms of a disease.

The following examples are presented in order to more fully illustrate certain embodiments of the invention. They should in no way, however, be construed as limiting the broad scope of the invention. One skilled in the art can readily devise many variations and modifications of the principles disclosed herein without departing from the scope of the invention.

EXAMPLES

Example 1

Preparation of Poly(Ricinoleic Acid-Sebacic Acid) Copolymer

Example 1.1

Preparation of Ricinoleic Acid from Castor Oil

Ricinoleic acid was obtained as described in U.S. Pat. No. 8,575,092, the content of which is hereby incorporated by reference. Specifically, castor oil was dissolved in 2 volumes of 2N KOH in ethanol at room temperature for a few hours with continuous stirring. The resulting potassium ricinoleate precipitate in ethanol was mixed with isopropyl ether to better separate the precipitate, and the mixture was allowed to separate. The precipitate slurry was centrifuged to separate the solids, and the solvent was decanted. The ricinoleic acid potassium salt was dispersed in iced 1N HCl solution and extracted with ethyl acetate. After solvent evaporation, a slightly yellow oil was obtained which contained 100% fatty acids of which at least 95% was ricinoleic acid as determined by gas chromatography.

Example 1.2

Activation of Sebacic Acid

Sebacic acid was activated by melt condensation to form poly(sebacic acid) (PSA) as described in U.S. Pat. No. 8,575,092, the content of which is hereby incorporated by reference. Specifically, sebacic acid was boiled in acetic anhydride for 20 minutes. The acetic anhydride was evaporated to dryness to obtain an off-white prepolymer of sebacic acid. PSA having a molecular weight of ~25,000 Da was prepared from the prepolymer by heating to 140° C. under high vacuum ($1.3 \times 10^{-1}$ mbar) for 3 hours thereby obtaining the PSA with the desired molecular weight.

Example 1.3

Preparation of Poly(Ricinoleic Acid-Sebacic Acid)(70:30) Copolymer

Poly(Ricinoleic Acid-Sebacic Acid)(70:30) copolymer was prepared according to the following procedure. Warm RA was added to the PSA prepolymer over 45 minutes. The mixture was heated to 167° C. and stirred for several hours until the reaction was completed (2.3% of free RA were detected using NMR monitoring). After cooling to 135° C., the mixture was treated with acetic anhydride and heated to reflux. After about 1 hour, the volatiles were distilled at ~80-100° C. (150-40 mbar). The final polymerization was performed at 140° C./30 mbar for about 4 hours until polymer with molecular weight of ~11,000-15,000 Da was obtained. The obtained polymer was cooled to 110-120° C., and transferred to closed glass bottles, flushed with $N_2$, and stoppered.

Example 2

Characterization of Poly(Ricinoleic Acid-Sebacic Acid) Copolymer

Example 2.1

Monitoring the Reactions using Different Routes of Synthesis

Poly (Ricinoleic Acid-Sebacic Acid) was synthesized using two different reaction conditions.

Reaction Condition 1:

The polymer was prepared as described in Krasko et al. (J. Polymer Science Part A: Polymer Chemistry 2003, 41, 1059). In particular, 35 g of Ricinoleic acid (RA; 85% pure; Fluka, Buch, Switzerland) and 15 g of the synthesized Polysebacic acid (PSA prepared from sebacic acid; 99% pure; Aldrich, Milwaukee, Wis.) were mixed. Temperature was raised to 120° C. The reaction mixture was stirred for 2 h in a close flask under nitrogen atmosphere to yield the prepolymer. Activation of the carboxylic end groups was achieved by dissolving the obtained prepolymer in acetic anhydride (Merck, Darmstadt, Germany; 1:0.5 w/v), refluxed at 140° C. for 30 min. Solvent (analytical-grade from Sigma-Aldrich (Rosh Haain, Israel) or Frutarom (Haifa, Israel)) was evaporated to dryness. The poly(ester anhydride) was prepared by melt condensation of the prepolymer over a period of 4 h at 140° C. under vacuum (10-15 mbar). Samples for NMR were collected after esterification (at the prepolymer stage) and after polymerization (when final polymer was obtained).

Reaction Condition 2:

Poly(RA-SA) was synthesized by gradual increase of temperature. 900 g of ricinoleic acid and 390 g PSA were heated under inert atmosphere at 140° C. for 3 h. The reaction mixture was then gradually heated to 165° C. Heating was continued at this temperature for 1 h. After 1 h, the temperature was raised to 175° C. and heating was continued for 4 h. Then, the mixture was cooled to about 135° C. 750 mL of acetic anhydride was added to this mixture and refluxed at about 140° C. for 1 h. The volatiles were distilled out under reduced pressure. The uniform mixture was subjected to melt condensation at 140° C. under vacuum of 15-30 mm Hg for 6 h. Samples were collected at regular intervals for analysis. The same procedure was used for synthesizing poly(RA-SA) at different weight ratios of PSA:RA.

The progress of the reactions was monitored focusing on the consumption of RA and formation of new ester bonds. After polymerization, the ratio of ester: anhydride bonds formed was further estimated. It is contemplated that the more RA-SA ester bonds, the more alternate RA-SA-RA-SA sequence of the polymer obtained. The differences were determined by $^1$H-NMR analysis. In order to monitor the reaction progress, the δ values of $^1$H NMR of pure PSA and poly RA oligoesters was initially determined.

Figure 2:
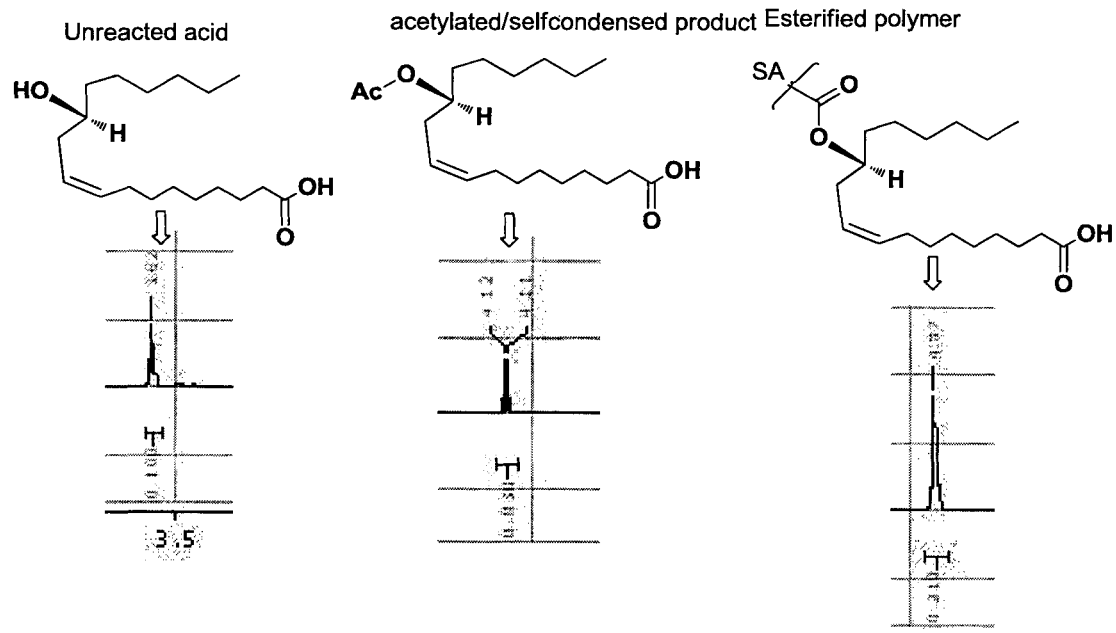
FIG. 2 shows the molecular structures and their corresponding chemical shifts of the proton used to quantify the formation of different products through $^1$H-NMR (500 MHz, CDCl$_3$).
Figure 3:
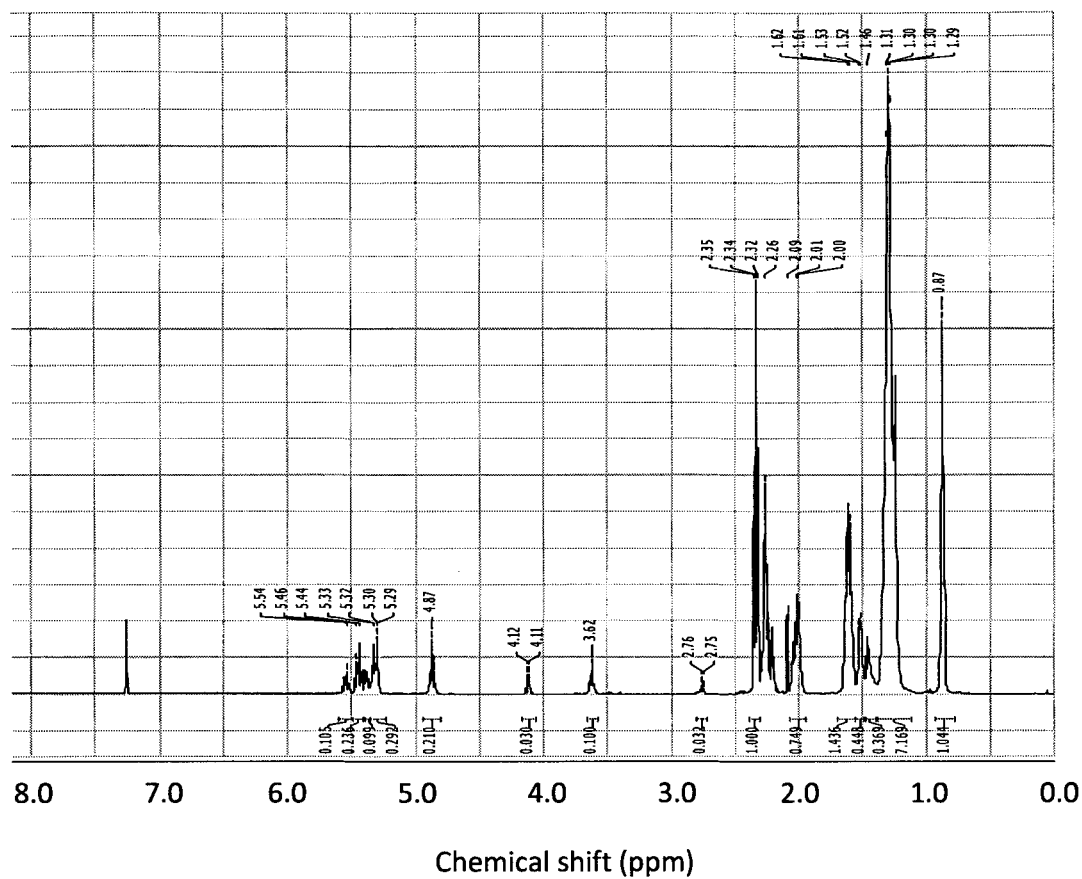
FIG. 3 shows the $^1$H-NMR spectrum of the prepolymer produced using Reaction Condition 1 after the esterification step. The spectrum shows about 29% of unreacted RA.
Figure 4:
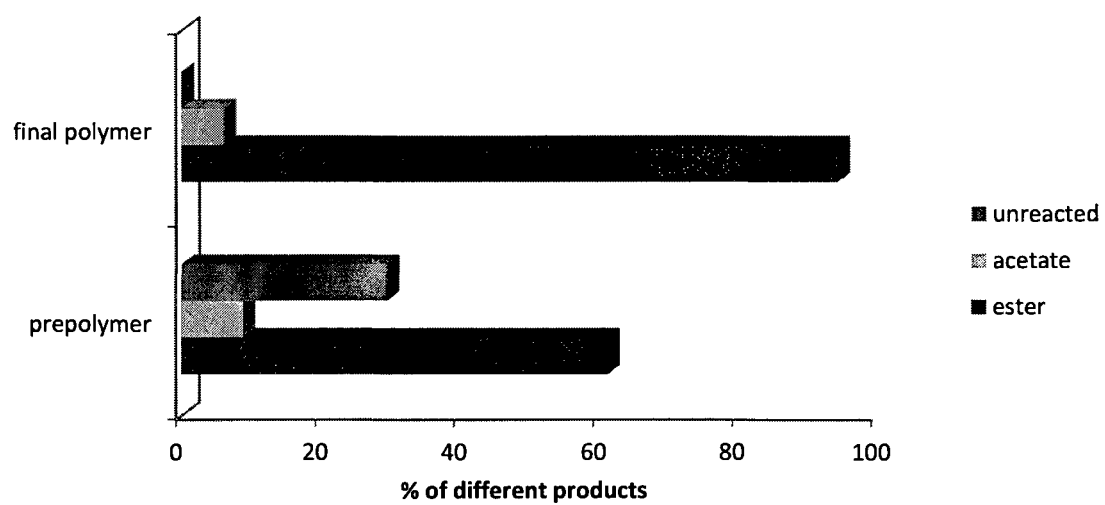
FIG. 4 shows a diagram of the ratio of integration of proton 'α' to the hydroxy group of RA as recorded by $^1$H-NMR at 500 MHz. The figure depicts the kinetics of conversion to different products of unreacted RA (top), acetate-RA (middle), and ester-polyester of PSA and RA (bottom) obtained by Reaction Condition 1. Prepolymer—the polymer obtained after the esterification step. Final polymer—the polymer obtained after melt condensation.

During the esterification step, the ester bonds formed between the hydroxyl groups of ricinoleic acid and the carboxylic acids resulted in the appearance of peak at δ 4.8 ppm. In the final polymer no acetylation of the free hydroxyl group of RA (a peak at δ 4.2 ppm) was observed. In order to simulate reaction conditions in which unreacted RA remains, RA (10 g) was added to boiling acetic anhydride (100 ml) for 30 min. The acetic anhydride was evaporated to dryness and the residue was analyzed by $^1$H-NMR and by GPC. It was found that RA converts to RA oligomers in the presence of acetic anhydride (FIG. 1). These oligomers may be incorporated into the RA-SA framework, mainly as diblock copolymers. The incorporation can be through ester or anhydride linkages appearing in $^1$H δ of 2.45 and 2.25, respectively. $^1$H-NMR spectra analysis focused on two types of protons, the single proton on carbon 9, the carbon bearing the —OH group in RA, and the two protons adjacent to the ester bonds (—$CH_2$—COO—CH—, δ=2.43 ppm) and anhydride bonds (—$CH_2$—COO—CO—$CH_2$—, δ=2.33 ppm) as shown in FIG. 2. The ratio of the different products was calculated by measuring the integration of the proton 'α' to the hydroxy group of RA as follows: 1. the proton of unreacted RA at δ~3.6 ppm; 2. the proton of the acetylated/self-condensed RA at δ~4.1 ppm; and 3. the proton of esterified polymer at δ~4.8 ppm. $^1$H NMR results (FIGS. 3 & 4) indicate that under Reaction Condition 1, 29% of added ricinoleic acid remained unreacted after the esterification step (before adding acetic anhydride). As detailed above, these 29% of unreacted RA formed RA oligomers. The ester: anhydride ratio was not affected (66%:34%) in the final polymer due to formation of self-condensed RA oligoesters. Accordingly, poly(SA-RA) formed by Reaction Condition 1, is composed of RA block chains and therefore of SA-SA anhydride oligomers along the polymer chain. This uneven distribution of anhydride and ester bonds along the polymer chain results in a polymer which is more sensitive to hydrolysis of the anhydride bonds as well as to anhydride interchange.

Figure 5A:
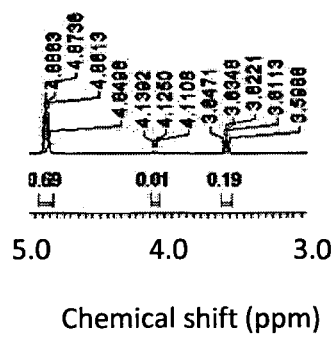
FIGS. 5A-5B show the ratio of the integration of proton 'α' to the hydroxy group of RA as recorded by $^1$H-NMR at 500 MHz depicting the kinetics of the conversion to different products.
Figure 5B:
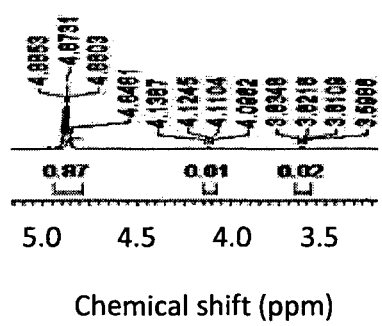
Figure 6:
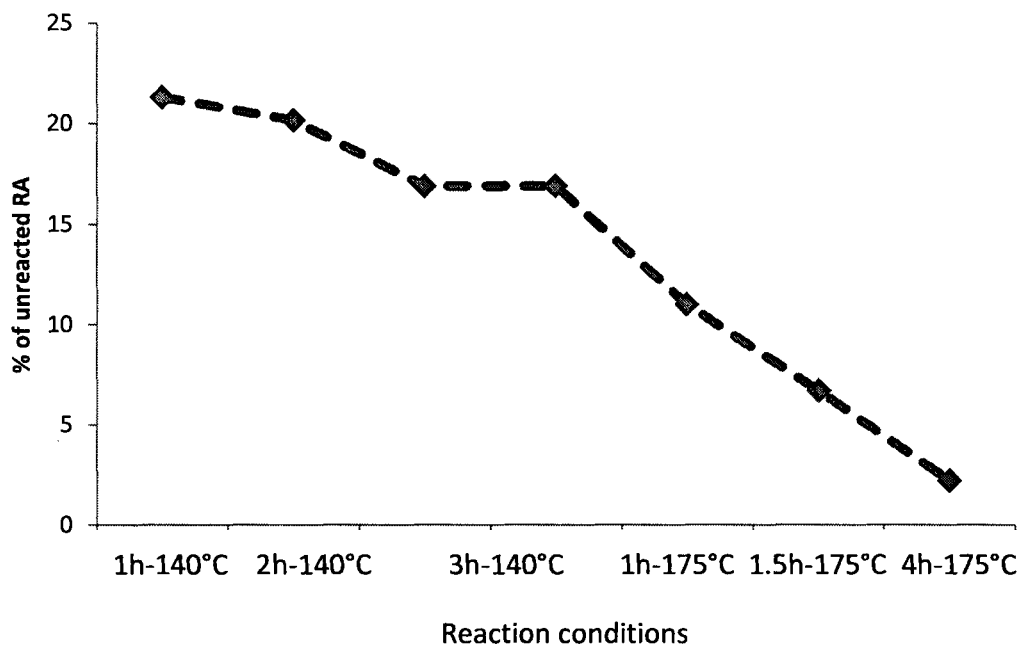
FIG. 6 shows a graph of the rate of consumption of RA using the synthesis route of the method disclosed herein as calculated from the integration of proton 'α' to the hydroxy group of RA recorded by $^1$H-NMR at 500 MHz.
Figure 7:
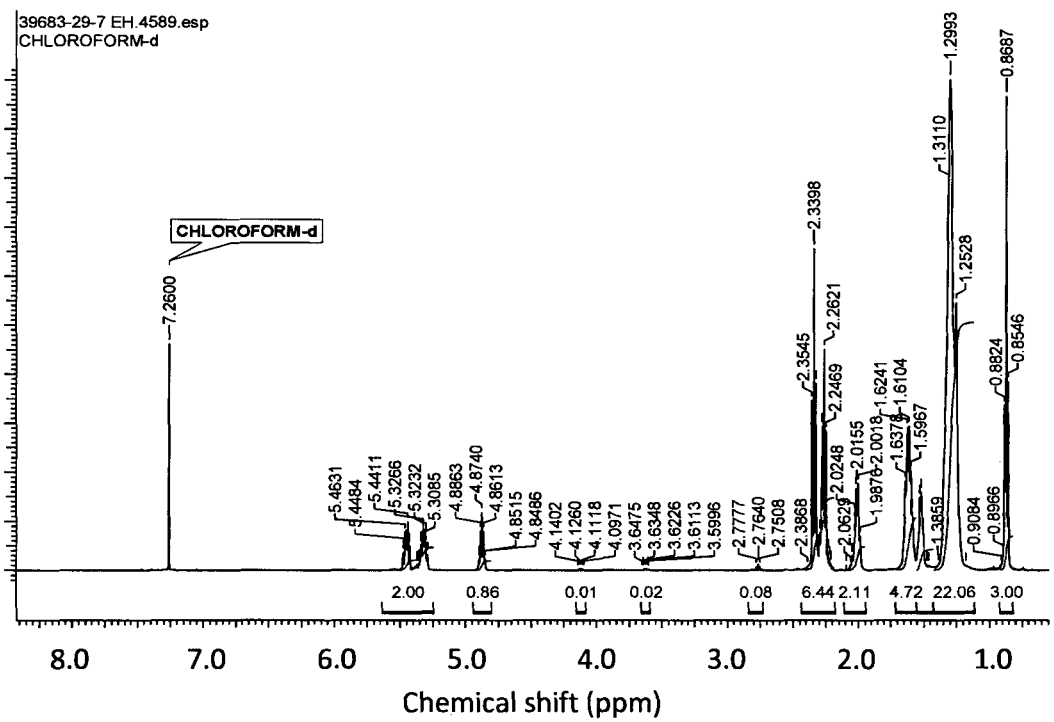
FIG. 7 shows the $^1$H-NMR spectrum of the prepolymer produced using Reaction Condition 2 showing about 2% of unreacted RA.
Figure 8:
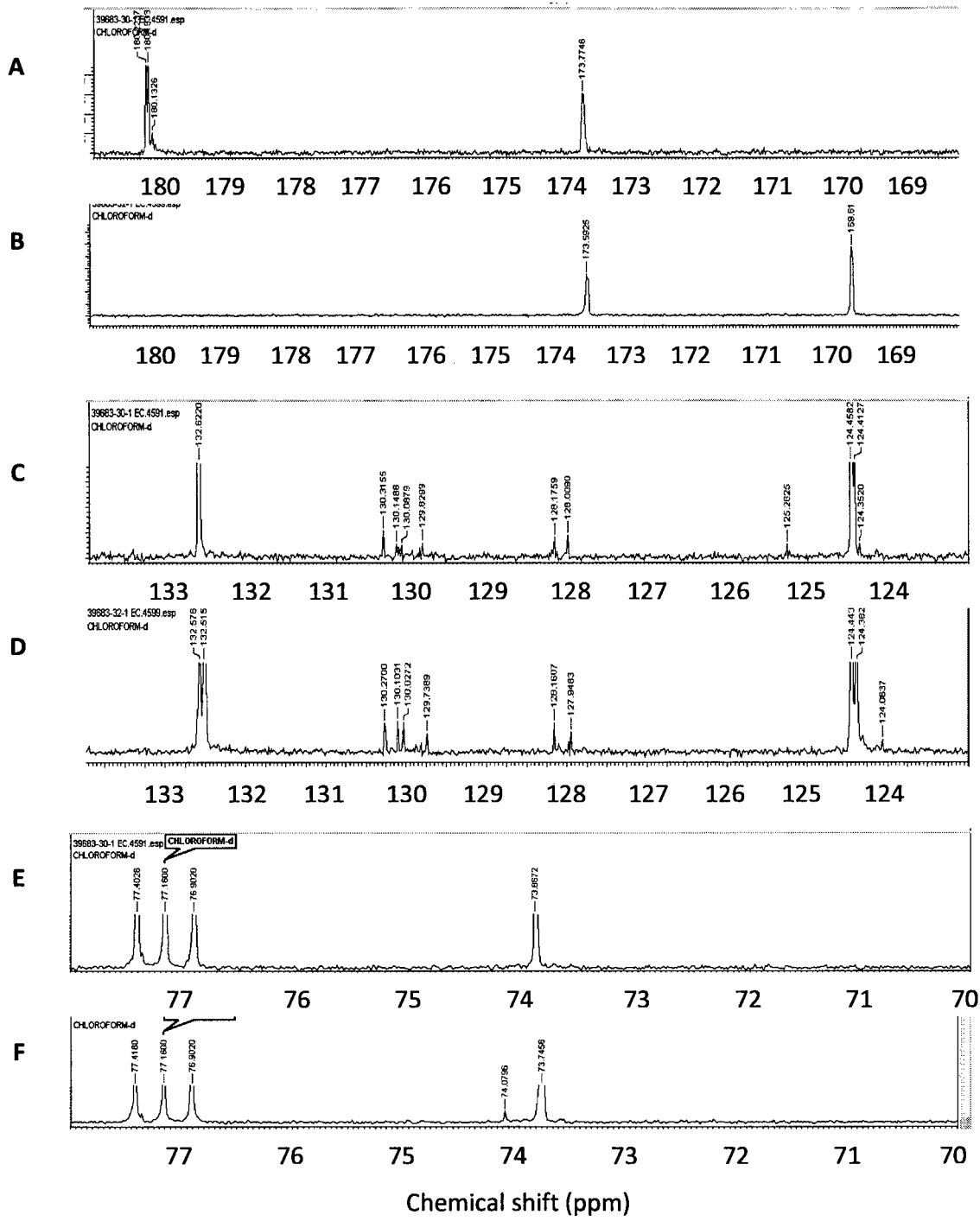
FIG. 8 shows the $^{13}$C NMR spectra for the prepolymer (panels A, C, and E) and the final polymer (panels B, D, and F) synthesized according to Reaction Condition 2. A&B: Carbonyl region; C&D: C=C region; and E&F: —CHOH region.
Figure 9A:
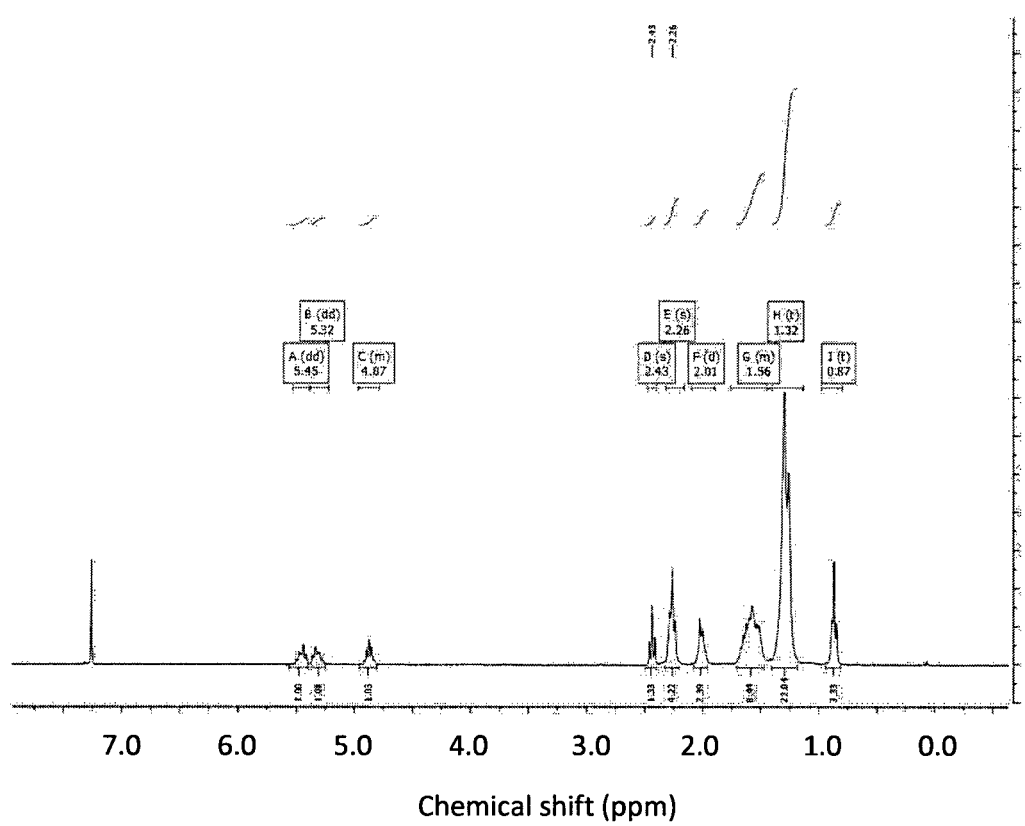
FIGS. 9A-9F show the $^1$H NMR spectra (300 MHz, CDCl$_3$) of the polymers prepared from RA-SA-RA trimer (9A and 9B); RA-SA dimer (9C and 9D); and mixture of RA-SA dimer and RA-SA-RA trimer (9E and 9F).
Figure 9B:
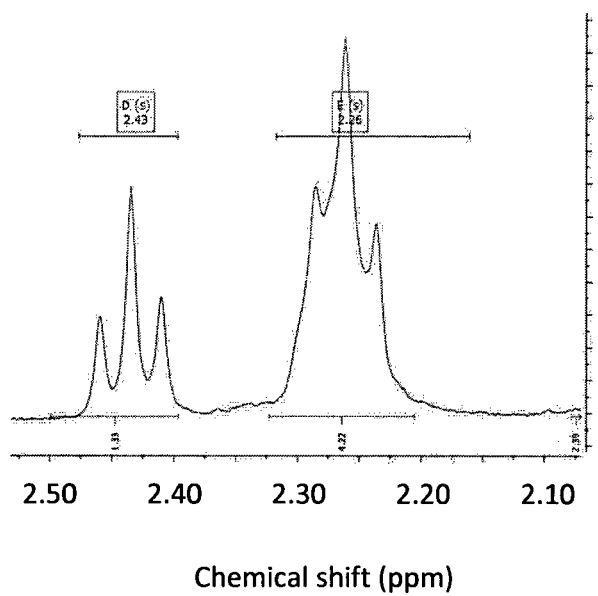
Figure 9C:
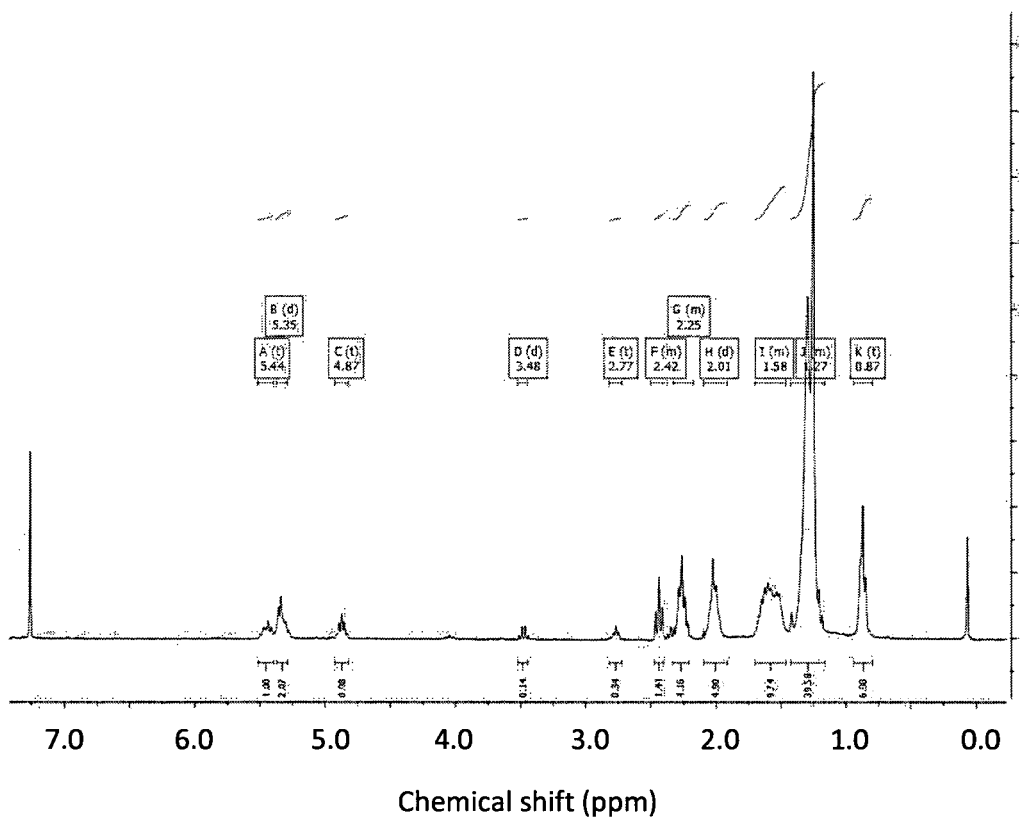
Figure 9D:
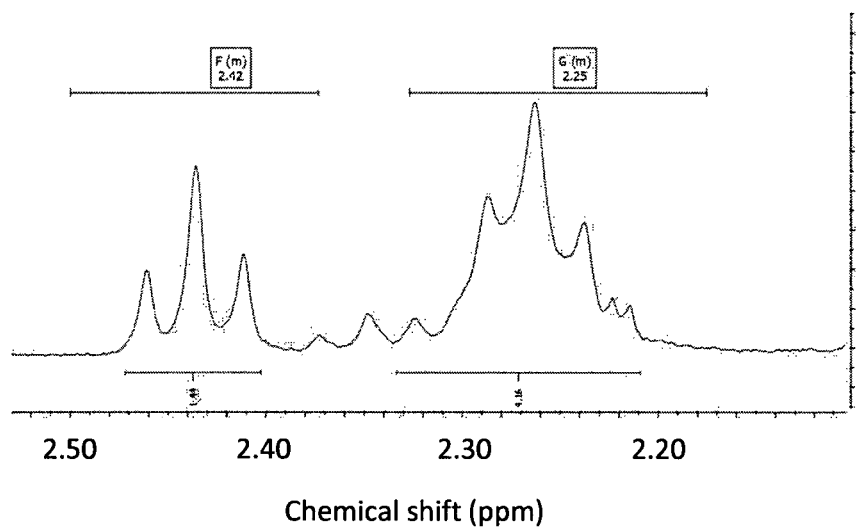
Figure 9E:
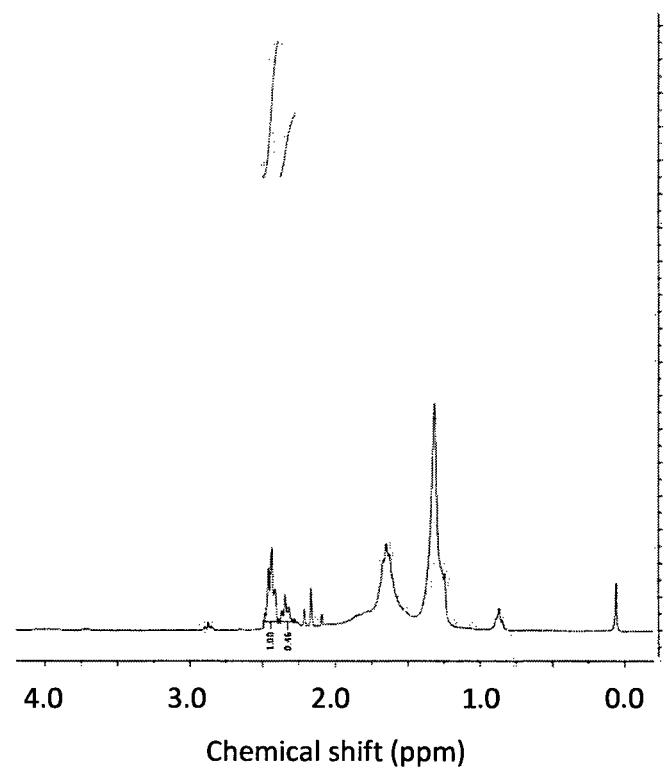
Figure 9F:
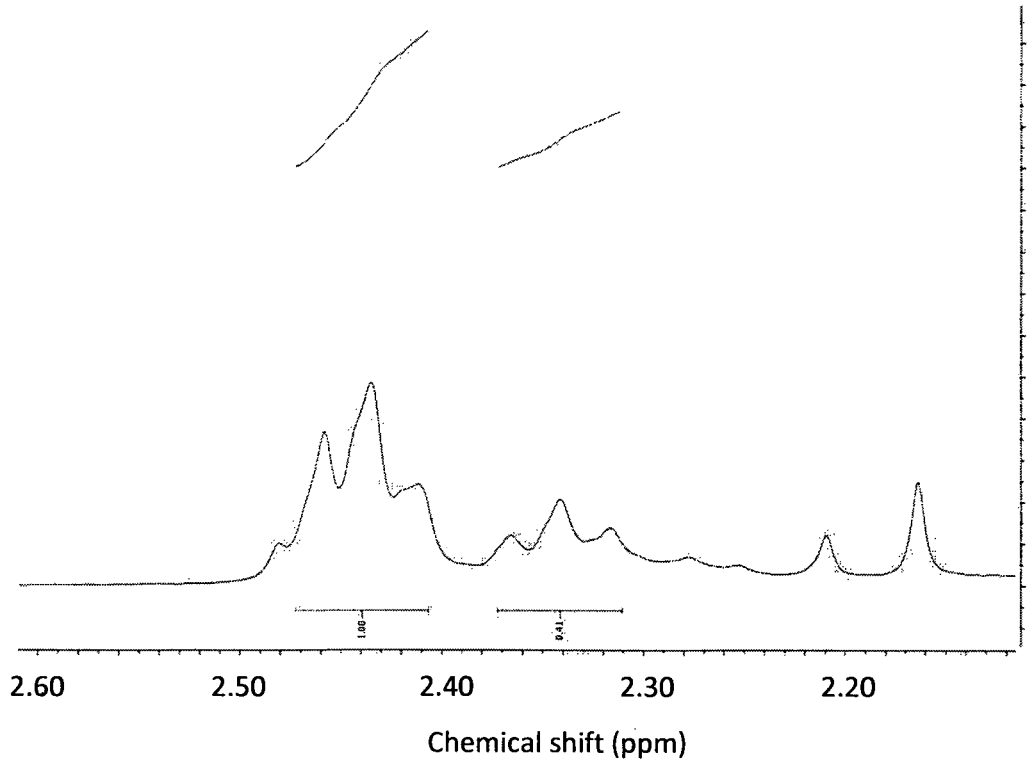

Using Reaction Condition 2 according to the embodiments disclosed herein, the relative ratio of the protons measured by the integration of proton 'α' to the hydroxy group of RA in the NMR spectra (500 MHz; FIG. 5) revealed that the RA is consumed gradually over a period of several hours. Finally, only 2.2% of RA that has not reacted remained (FIGS. 6 & 7). A small amount of acetylated RA (about 1.1%) was observed. The prepolymer (before polycondensation) and final polymer were sampled and their $^{13}$C NMR was also recorded (FIG. 8). The comparison was performed in 3 areas: 160-180 ppm assigned to carboxyls, 135-120 ppm assigned to double bonds and 75-70 ppm assigned to free hydroxylic groups. The carboxylic acid shows peaks at δ~180 ppm, esters at 173.6 ppm and anhydrides at 169.6 ppm. Observation of the two alkenyl carbons at 124.5 and 132.6 ppm in the prepolymer and final polymer, respectively, revealed that significant incorporation of RA into the final polymer occurred. In particular, the peak at δ 71.7 ppm which is assigned to —CHOH carbon in RA was not observed in the final polymer, whereas the esterified RA peak at δ 73.9 ppm did show. It is thus concluded that no significant residual unreacted RA exists in the prepolymer and therefore no significant incorporation of RA oligoesters in the RA-SA polymeric framework.

Example 2.2

Characterization of Intermediates

In order to characterize the RA-SA-RA trimer and RA-SA dimer intermediates after the reaction between RA and PSA, the RA-SA-RA and RA-SA intermediates were isolated by preparative column chromatography through gradual elution with 5-10% EtOAc:hexane. The structures of the intermediates were confirmed by $^1$H NMR and mass spectrometry. No other spots were revealed using TLC, except those assigned to RA-SA dimer and RA-SA-RA trimer.

RA-SA-RA: $^1$H NMR (300 MHz, CDCl$_3$) δ 5.43 (m, 1H), 5.33 (m, 1H), 4.87 (m, 1H), 2.28 (m, 6H), 2.02 (m, 3H), 1.60 (m, 6H), 1.29 (d, 24H), 0.89 (t, 3H). ESI MS (m/z): [MW]-calculated for C$_{46}$H$_{82}$O$_8$, 762.60; found 761.

RA-SA-RA Trimer
$^1$H NMR (300 MHz, CDCl$_3$) δ 5.45 (dd, J=18.1, 7.4 Hz, 1H), 5.32 (dd, J=17.7, 7.9 Hz, 1H), 4.96-4.78 (m, 1H), 2.43 (s, 1H), 2.26 (s, 4H), 2.01 (d, J=7.7 Hz, 2H), 1.76-1.40 (m, 9H), 1.32 (t, J=24.2 Hz, 22H), 0.87 (t, J=6.4 Hz, 3H).

RA-SA Dimer
$^1$H NMR (300 MHz, CDCl$_3$) δ 5.44 (s, 17H), 5.35 (d, J=5.7 Hz, 35H), 4.98-4.80 (m, 15H), 2.77 (s, 7H), 2.30 (dt, J=24.0, 7.3 Hz, 84H), 2.01 (d, J=8.3 Hz, 71H), 1.69-1.47 (m, 91H), 1.44-1.16 (m, 587H), 0.86 (d, J=6.5 Hz, 87H), 0.07 (s, 33H).

RA-SA Polymer
$^1$H NMR (300 MHz, CDCl$_3$) δ 5.44 (t, J=8.7 Hz, 12H), 5.35 (d, J=5.8 Hz, 25H), 4.87 (t, J=6.2 Hz, 12H), 3.48 (d, J=7.0 Hz, 2H), 2.77 (t, J=5.9 Hz, 4H), 2.50-2.37 (m, 17H), 2.33-2.18 (m, 50H), 2.01 (d, J=7.5 Hz, 59H), 1.70-1.46 (m, 117H), 1.42-1.16 (m, 475H), 0.87 (t, J=5.0 Hz, 73H).

After isolating the trimer (RA-SA-RA) and dimer (RA-SA), the intermediates were individually polymerized. Both the polymer resulting from the trimer RA-SA-RA and the polymer resulting from the dimer RA-SA showed significant excess (-twice) of anhydride formation. On the other hand, a polymer synthesized from a mixture of RA-SA and RA-SA-RA (original mix of 70:30, RA:SA) resulted in excess polyester as shown in FIG. 9.

Three different ratios of RA and SA were evaluated as follows: RA:SA—70:30; 50:50; and 30:70. For RA:SA 70:30, the relative amount of the trimer (RA-SA-RA) is significantly higher than the dimer (RA-SA). At RA:SA ratios of 50:50 and 30:70, the relative amount of trimer consistently decreased.

Figure 10A:
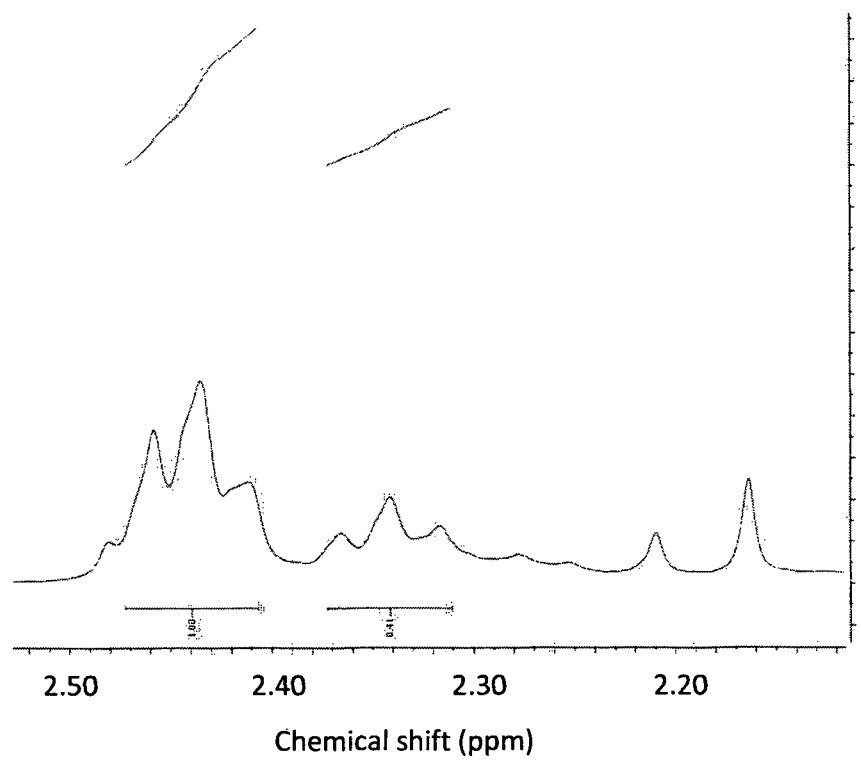
FIGS. 10A-10C show the relative percentages of polyesters formed in the final polymer with respect to polyanhydride using different RA:SA weight ratios. The relative percentages were calculated by integrating the peaks of 'α' protons of the ester and anhydride bonds, as recorded in $^1$H NMR spectroscopy. Weight ratio 70:30 RA:SA, 84% polyester formed (10A); weight ratio 50:50 RA:SA, 70% polyester formed (10B); and weight ratio 30:70 RA:SA, 51% polyester formed (10C).
Figure 10B:
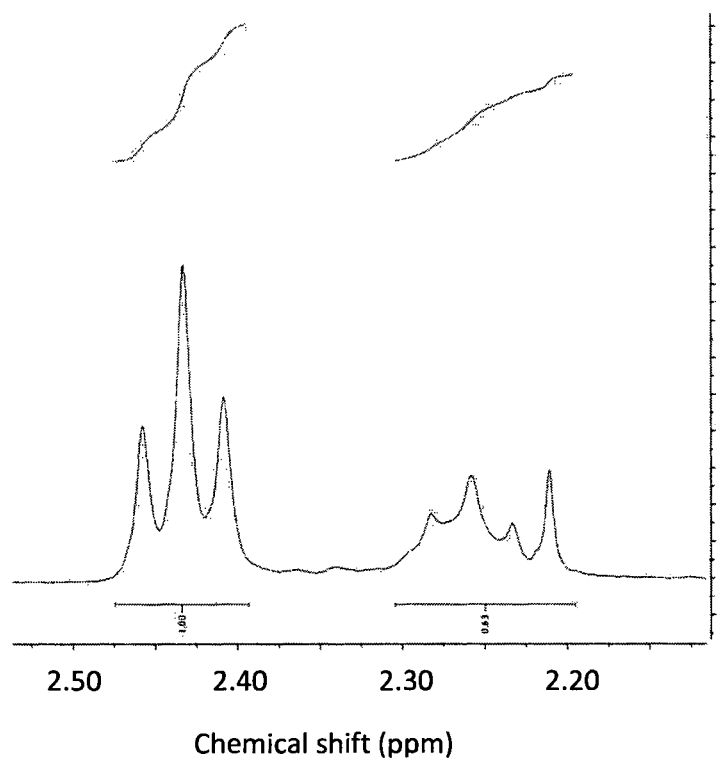
Figure 10C:
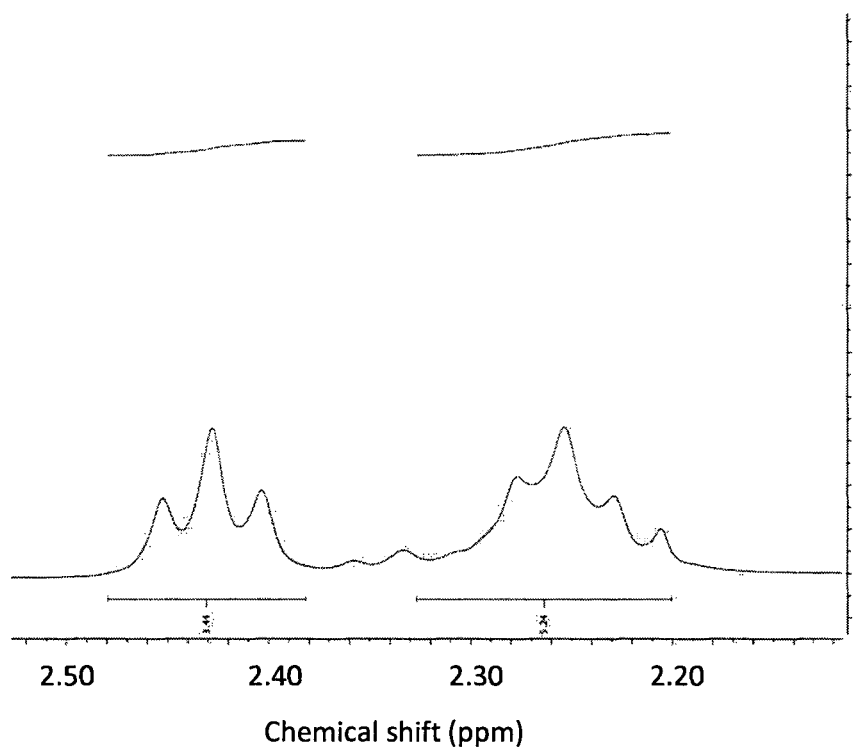

The relative ratio of the polyester to polyanhydride at different ratios of RA and SA was also evaluated. A consistent increase in polyester formation was observed as the ratio of RA increased (FIG. 10). The results are outlined in Table 1.

Thus, the route of synthesis of the polymer according to the methods disclosed herein provides poly(RA-SA) having alternating or semi-alternating units of ricinoleic and sebacic acids as well as alternating or semi-alternating ester and anhydride bonds along the polymer chain.

Example 3

Stabilization Measurements of Poly(Ricinoleic Acid-Sebacic Acid)(70:30) Copolymer Example 3.1

Comparative Storage Stability of Poly(RA-SA) 70:30 Prepared by Reaction Conditions 1 and 2

Samples (100 mg) of the polymers prepared by Reaction Conditions 1 and 2 as detailed in Example 2 are placed in a glass vial sealed with septa and stored at refrigeration and at room temperatures. At each time point, 1, 4, 8, and 12 weeks, one vial of each polymer is analyzed for molecular weight by GPC.

Example 3.2

The Stability of the Poly(RA-SA) 70:30 in Regular and Accelerated Storage Conditions The stability of the poly(ricinoleic acid-sebacic acid)(70:30) copolymer produced as described in Example 1 was assessed with or without 10% and 20% API. Samples were placed in glass syringes, packed in sealed aluminum vacuum bags, irradiated with γ-irradiation and stored for 18 months at normal, intermediate, and accelerated conditions, namely −20° C.±5° C., 5° C.±3° C., and 25° C.±2° C./60% RH±5% RH, respectively. Measurements of water content using Karl Fisher (KF) Coulometer, and measurements of molecular weight (MW) and polydispersity index (PDI) were conducted at t=0 and after 1, 3, 6, 9, 12 and 18 months. The results are presented in Table 2:

TABLE 1

Comparison of copolymer characteristics using different synthetic routes, ratio of monomers and intermediates

| Description of the synthesized polymer | | % unreacted RA in the prepolymer | % of polyester | % of polyanhydride | Molecular weight [Da] |
|---|---|---|---|---|---|
| Polymer synthesized according to Reaction Condition 1 | | 29 | 66 | 33 | 6494 |
| Polymer synthesized according to Reaction Condition 2 | RA:SA 70:30 | Traces | 80 | 20 | 14142 |
| | RA:SA 50:50 | Traces | 70 | 30 | 16408 |
| | RA:SA 30:70 | Traces | 51 | 49 | 16369 |
| Polymer synthesized only through RA-SA-RA subunits | | Not observed | 33.33 | 66.66 | 9864 |
| Polymer synthesized only through RA-SA subunits | | Traces | 33.33 | 66.66 | 5576 |

TABLE 2

Effect of storage conditions on water content, molecular weight and polydispersity index (PDI) of the polymer

| Storage Conditions | Sampling time | API content | Water content (KF) | Polymer MW (GPC) | Polymer PDI (GPC) |
|---|---|---|---|---|---|
| — | t = 0 | 0 | 0.00000% | 13582 | 3.8 |
| — | t = 0 | 10% | 0.00000% | 15211 | 3.8 |
| — | t = 0 | 20% | 0.00000% | 16278 | 3.9 |
| −20° C. | 1 month | 0 | 0.00030% | 15367 | 3.5 |
| −20° C. | 3 months | 0 | 0.00800% | 12331 | 3.1 |
| −20° C. | 6 months | 0 | 0.02000% | 16920 | 3.5 |
| −20° C. | 9 months | 0 | 0.02000% | 14029 | 3.2 |
| −20° C. | 12 months | 0 | 0.02000% | 13330 | 3.7 |
| −20° C. | 18 months | 0 | 0.00000% | 14905 | 4.6 |
| −20° C. | 1 month | 10% | 0.00030% | 15794 | 3.8 |
| −20° C. | 3 months | 10% | 0.00000% | 13741 | 3.1 |
| −20° C. | 6 months | 10% | 0.00000% | 16267 | 3.5 |
| −20° C. | 9 months | 10% | NA | NA | NA |
| −20° C. | 12 months | 10% | 0.02000% | 15741 | 3.6 |
| −20° C. | 18 months | 10% | 0.00000% | 16017 | 5.0 |
| −20° C. | 1 month | 20% | 0.00200% | 16582 | 3.7 |
| −20° C. | 3 months | 20% | 0.00000% | 14397 | 3.1 |
| −20° C. | 6 months | 20% | 0.00000% | 16817 | 3.7 |
| −20° C. | 9 months | 20% | 0.02000% | 15257 | 3.2 |
| −20° C. | 12 months | 20% | 0.05000% | 16639 | 3.5 |
| −20° C. | 18 months | 20% | 0.00000% | 16817 | 5.4 |
| 5° C. | 1 month | 0 | 0.00800% | 15761 | 3.6 |

TABLE 2-continued

Effect of storage conditions on water content, molecular weight and polydispersity index (PDI) of the polymer

| Storage Conditions | Sampling time | API content | Water content (KF) | Polymer MW (GPC) | Polymer PDI (GPC) |
|---|---|---|---|---|---|
| 5° C. | 3 months | 0 | 0.00000% | 13296 | 3.3 |
| 5° C. | 6 months | 0 | 0.03000% | 15972 | 3.8 |
| 5° C. | 9 months | 0 | 0.00000% | 13806 | 3.2 |
| 5° C. | 12 months | 0 | 0.00000% | 12903 | 2.2 |
| 5° C. | 18 months | 0 | 0.00000% | 14473 | 4.7 |
| 5° C. | 1 month | 10% | 0.00000% | 15630 | 4.0 |
| 5° C. | 3 months | 10% | 0.02000% | 13792 | 3.1 |
| 5° C. | 6 months | 10% | 0.00000% | 16280 | 3.9 |
| 5° C. | 9 months | 10% | 0.00000% | 14005 | 3.3 |
| 5° C. | 12 months | 10% | 0.00000% | 14783 | 3.6 |
| 5° C. | 18 months | 10% | 0.00000% | 15130 | 5.0 |
| 5° C. | 1 month | 20% | 0.00900% | 16505 | 3.7 |
| 5° C. | 3 months | 20% | 0.00000% | 13324 | 3.2 |
| 5° C. | 6 months | 20% | 0.00000% | 16762 | 3.9 |
| 5° C. | 9 months | 20% | 0.00000% | 15119 | 3.2 |
| 5° C. | 12 months | 20% | 0.00000% | 16431 | 3.5 |
| 5° C. | 18 months | 20% | 0.00000% | 15804 | 5.1 |
| 25° C./60% RH | 1 month | 0 | 0.00800% | 15852 | 3.6 |
| 25° C./60% RH | 3 months | 0 | 0.04000% | 12741 | 3.3 |
| 25° C./60% RH | 6 months | 0 | 0.02000% | 15708 | 3.6 |
| 25° C./60% RH | 9 months | 0 | 0.00800% | 13490 | 3.2 |
| 25° C./60% RH | 12 months | 0 | 0.02000% | 13212 | 3.5 |
| 25° C./60% RH | 18 months | 0 | 0.01000% | 15708 | 4.6 |
| 25° C./60% RH | 1 month | 10% | 0.00200% | 15699 | 3.8 |
| 25° C./60% RH | 3 months | 10% | 0.00000% | 13324 | 3.2 |
| 25° C./60% RH | 6 months | 10% | 0.00000% | 15348 | 3.9 |
| 25° C./60% RH | 9 months | 10% | 0.00000% | 13776 | 3.2 |
| 25° C./60% RH | 12 months | 10% | 0.00000% | 12889 | 3.7 |
| 25° C./60% RH | 18 months | 10% | 0.00000% | 13916 | 4.9 |
| 25° C./60% RH | 1 month | 20% | 0.00100% | 16033 | 4.0 |
| 25° C./60% RH | 3 months | 20% | 0.00000% | 13699 | 3.6 |
| 25° C./60% RH | 6 months | 20% | 0.00000% | 16265 | 3.8 |
| 25° C./60% RH | 9 months | 20% | 0.00000% | 14396 | 3.2 |
| 25° C./60% RH | 12 months | 20% | 0.00000% | 14786 | 4.1 |
| 25° C./60% RH | 18 months | 20% | 0.00000% | 16265 | 5.0 |

* NA = not available

Figure 11A:
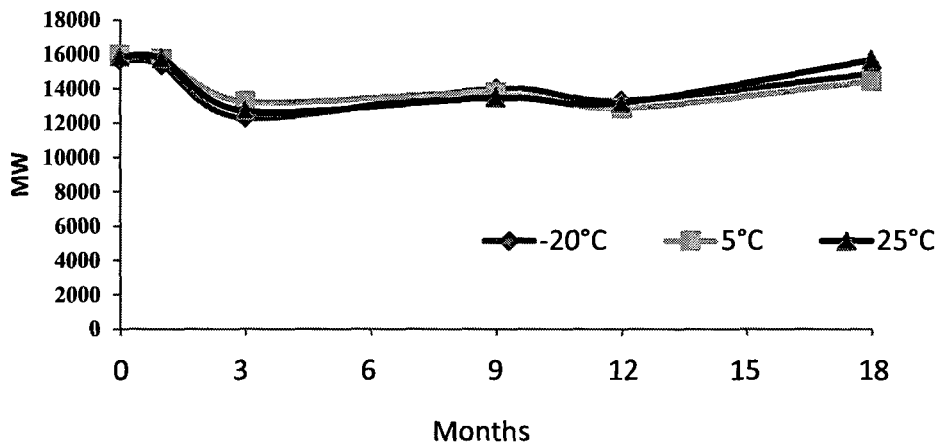
FIGS. 11A-11C show stability studies for (RA-SA) alternating or semi-alternating copolymer.

Changes in molecular weight of the synthesized RA-SA polymer were monitored for up to 18 months, under the following conditions: −20° C., 5° C., and at 25° C. and 60% relative humidity (RH). The polymer was stable at 25° C. and 60% RH for 18 months with molecular weight remaining substantially constant (FIG. 11A). This remarkable stability, as compared to previously reported polyanhydrides which are unstable and should be stored at −20° C., provides the ease of handling, formulating, and storage over longer periods.

Figure 11B:
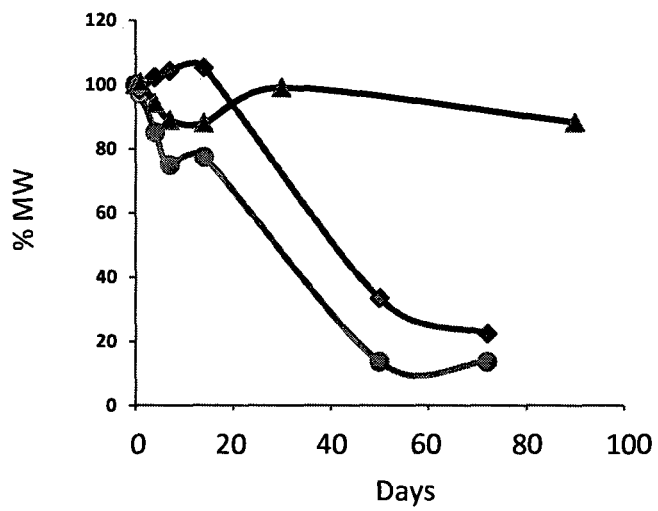
Figure 11C:
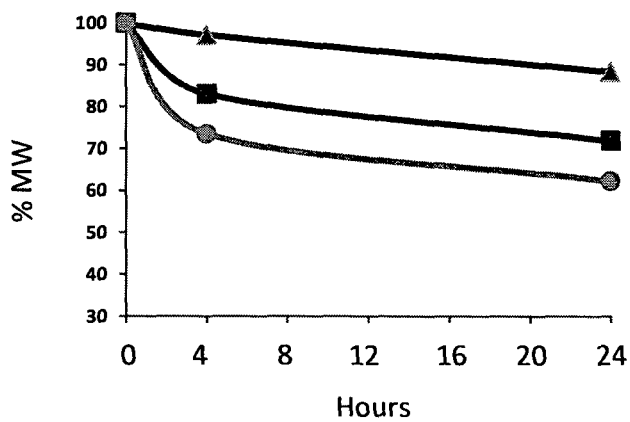

FIGS. 11B and 11C show a comparison of the stability of the three polymers (PSA, previously synthesized RA-SA polymer according to Krasko et al. J. Polymer Science Part A: Polymer Chemistry 2003, 41, 1059, and polymer synthesized though the currently disclosed method) over periods of up to 100 days at 25° C. and up to 24 hours in chloroform, respectively.

The results presented herein show that the polymer produced by the hitherto known methods (Krasko, et al. J. Cont. Release, 2007, 117, 90 and Krasko et al. J. Polymer Science Part A: Polymer Chemistry 2003, 41, 1059) as well as polysebacic acid substantially degrade at room temperatures with approximately 80% drop in molecular weight after 70 days (FIG. 11B). In contrast, the polymer produced by the method disclosed herein remained stable with no significant change in its molecular weight. It is believed that the alternating architecture of the polymer framework (RA-SA-RA) which is afforded by the method disclosed herein provides improved stability and hinders hydrolytic cleavage and anhydride interchange. Such interchange can result in shorter fragments and sharp declines in the molecular weights. Whereas the hydrolysis pattern of the alternating copolymer in an aqueous medium is similar to other polyanhydrides, anhydride interchange in the alternating RA-SA copolymer, as evident by the behavior of the polymer in chloroform (FIG. 11C), is significantly hindered due to polymer's dangling RA side chains which impart stability to the entire polymer. In addition, polymer properties were essentially unaffected by γ-irradiation at a dose of 2.5 Mrad showing similar molecular weights both before and after irradiation.

Unless defined otherwise, all technical and scientific terms used herein have the same meanings as commonly understood by one of skill in the art. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

The invention claimed is:

1. A method of preparing a poly(ester-anhydride) copolymer having alternating or semi-alternating ester and anhydride bonds comprising a structure of Formula (1)

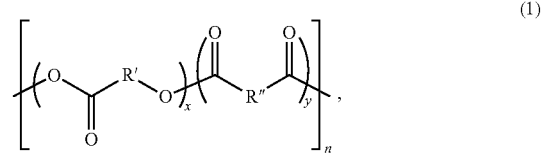

wherein R' and R" are independently selected from linear or branched $C_1$-$C_{40}$ alkyl, $C_2$-$C_{40}$ alkenyl, and $C_2$-$C_{40}$ alkynyl, and wherein each x and y is independently an integer from 1 to 5 provided that x+y is not greater than 6, and n is an integer from about 2 to about 1,000, the method comprising the steps of:

a) obtaining an activated compound of Formula (4)

b) reacting the activated compound of Formula (4) of step (a) with a compound of Formula (3)

to give a repeating unit comprising a compound of Formula (1a)

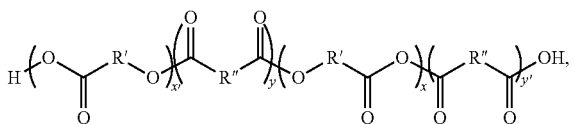
(1a)

wherein each x' and y' is independently an integer from 0 to 5 provided that x'+y' is not greater than 6; and c) converting the repeating unit of step (b) to an alternating or semi-alternating poly(ester-anhydride) copolymer of Formula (1).

2. The method of claim 1, wherein the compound of Formula (3) is ricinoleic acid and the compound of Formula (4) is sebacic acid.

3. The method of claim 1, wherein x and y, independently for each occurrence, is an integer selected from 1 and 2.

4. The method of claim 3, wherein reacting the activated compound of Formula (4) with a compound of Formula (3) gives a repeating unit comprising at least one of a compound of Formula (5), a compound of Formula (6) and a mixture thereof

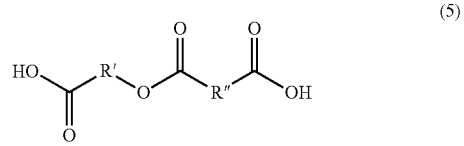
(5)

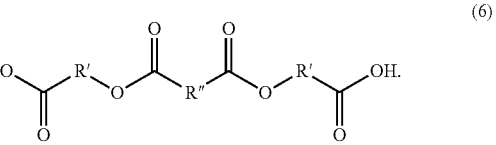
(6)

5. The method of claim 1, wherein obtaining an activated compound of Formula (4) comprises treating a compound of Formula (4) with an activating agent selected from the group consisting of acetic anhydride, propionic anhydride, phosgene, diphosgene, oxalyl chloride, acetyl chloride and thionyl chloride.

6. The method of claim 5, wherein the activating agent is acetic anhydride and the activated compound of Formula (4) is a polyanhydride of Formula (4p)

Formula (4p)

wherein R" is as defined in claim 1 and n' is integer from about 2 to about 500.

7. The method of claim 1, wherein the compound of Formula (3) is reacted with the activated compound of Formula (4) until at least 90% of the compound of Formula (3) is consumed.

8. The method of claim 1, wherein the compound of Formula (3) and the activated compound of Formula (4) are reacted under conditions suitable to substantially consume all of the compound of Formula (3), wherein the conditions comprise heating at a temperature of about 120-200° C., exposure to a vacuum, use of a catalyst or a combination thereof.

9. The method of claim 1, wherein step (c) comprises treating the reaction mixture with an activating agent under conditions suitable to form the poly(ester-anhydride) copolymer of Formula (1), wherein the activating agent is selected from the group consisting of acetic anhydride, propionic anhydride, phosgene, diphosgene, oxalyl chloride, acetyl chloride and thionyl chloride; or wherein the conditions suitable to form the poly(ester-anhydride) copolymer of Formula (1) comprise heating at a temperature of about 100-200° C., exposure to a vacuum of from about 15 to about 30 mmHg, or a combination thereof.

10. A poly(ester-anhydride) copolymer having alternating or semi-alternating ester and anhydride bonds comprising a structure of Formula (1)

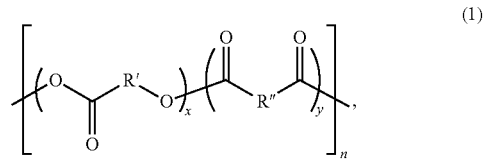
(1)

wherein the copolymer is formed by monomers of Formulae (3) and (4) at a molar ratio of 2:1:

(3)

(4)

wherein the copolymer comprises a repeating unit comprising a monomer of Formula (3), a monomer of Formula (4), and a monomer of Formula (3) linked by two consecutive ester bonds, wherein R' and R" are independently selected from linear or branched $C_1$-$C_{40}$ alkyl, $C_2$-$C_{40}$ alkenyl, and $C_2$-$C_{40}$ alkynyl, and wherein each x and y is independently an integer from 1 to 5 provided that x+y is not greater than 6, and n is an integer from about 2 to about 1,000.

11. The copolymer of claim 10, wherein the monomers of Formula (3) comprise ricinoleic acid and the monomers of Formula (4) comprise sebacic acid.

12. The copolymer of claim 10 which is stable for at least 6 months at room temperatures.

13. A composition comprising the copolymer of claim 10 and at least one agent, wherein the at least one agent is a pharmaceutical agent, a diagnostic agent, a cosmetic agent or a nutraceutical agent.

14. A poly(ester-anhydride) copolymer having alternating or semi-alternating ester and anhydride bonds comprising a structure of Formula (1)

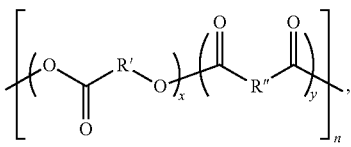

wherein the copolymer is formed by monomers of Formulae (3) and (4) at a molar ratio of 1.5:1:

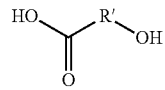

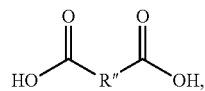

wherein the copolymer comprises two repeating units, wherein the first repeating unit comprises a monomer of Formula (3), a monomer of Formula (4), and a monomer of Formula (3) linked by two consecutive ester bonds, and wherein the second repeating unit comprises a monomer of Formula (3) and a monomer of Formula (4) linked by an ester bond, wherein R' and R" are independently selected from linear or branched $C_1$-C40 alkyl, $C_2$-$C_{40}$ alkenyl, and $C_2$-$C_{40}$ alkynyl, and wherein each x and y is independently an integer from 1 to 5 provided that x+y is not greater than 6, and n is an integer from about 2 to about 1,000.

15. The copolymer of claim 14, wherein the ratio between the first repeating unit and the second repeating unit is about 1:1.

16. The copolymer of claim 14, comprising an anhydride bond between repeating units, wherein the repeating units are arranged in the copolymer in an alternating or semi-alternating order.

17. The copolymer of claim 14, wherein the monomers of Formula (3) comprise ricinoleic acid and the monomers of Formula (4) comprise sebacic acid.

18. The copolymer of claim 14 which is stable for at least 6 months at room temperatures.

19. A composition comprising the copolymer of claim 14 and at least one agent, wherein the at least one agent is a pharmaceutical agent, a diagnostic agent, a cosmetic agent or a nutraceutical agent.

* * * * *